US008513392B2

(12) United States Patent
Berti

(10) Patent No.: US 8,513,392 B2
(45) Date of Patent: Aug. 20, 2013

(54) CONJUGATION OF STREPTOCOCCAL CAPSULAR SACCHARIDES

(75) Inventor: Francesco Berti, Siena (IT)

(73) Assignee: Novartis Vaccines and Diagnostics SRL, Siena (IT)

( * ) Notice: Subject to any disclaimer, the term of this patent is extended or adjusted under 35 U.S.C. 154(b) by 1036 days.

(21) Appl. No.: 11/883,614

(22) PCT Filed: Feb. 1, 2006

(86) PCT No.: PCT/IB2006/000756
§ 371 (c)(1),
(2), (4) Date: Mar. 18, 2008

(87) PCT Pub. No.: WO2006/082530
PCT Pub. Date: Aug. 10, 2006

(65) Prior Publication Data
US 2009/0043077 A1  Feb. 12, 2009

(30) Foreign Application Priority Data
Feb. 1, 2005   (GB) .................................. 0502095.3

(51) Int. Cl.
*A61K 39/09* (2006.01)
(52) U.S. Cl.
USPC ... 530/402; 530/363; 424/193.1; 424/197.11; 424/194.1
(58) Field of Classification Search
None
See application file for complete search history.

(56) References Cited

U.S. PATENT DOCUMENTS

| 4,356,170 A * | 10/1982 | Jennings et al. ........... 424/194.1 |
| 4,761,283 A * | 8/1988 | Anderson .................. 424/194.1 |
| 4,923,803 A * | 5/1990 | Izumori et al. ................... 435/26 |
| 5,795,580 A * | 8/1998 | Jennings et al. ........... 424/244.1 |
| 5,993,825 A * | 11/1999 | Jennings et al. ........... 424/244.1 |
| 6,225,462 B1 * | 5/2001 | Berry et al. ................. 536/123.1 |
| 6,248,570 B1 * | 6/2001 | Michon et al. ................ 435/101 |
| 6,426,074 B1 * | 7/2002 | Michel et al. .............. 424/244.1 |
| 6,573,245 B1 * | 6/2003 | Marciani ........................ 514/25 |
| 6,656,472 B1 * | 12/2003 | Chong et al. ............... 424/193.1 |

(Continued)

FOREIGN PATENT DOCUMENTS

| WO | 92/02817 | * 2/1992 |
| WO | WO9406467 | 3/1994 |
| WO | WO03007985 | 1/2003 |
| WO | WO2004011027 | 2/2004 |

OTHER PUBLICATIONS

Paoletti, LC et al, the Journal of Biological Chemistry, vol. 265(30), Oct. 25, pp. 18278-18283, An oligosaccharide-Tetanus Toxoid conjugate vaccine against type III Group B Streptococcus.*

(Continued)

*Primary Examiner* — Albert Navarro
*Assistant Examiner* — Ginny Portner
(74) *Attorney, Agent, or Firm* — Banner & Witcoff, Ltd.

(57) ABSTRACT

Three conjugation methods for use with the capsular saccharide of *Streptococcus agalactiae*. In the first method, reductive animation of oxidized sialic acid residue side chains is used, but the aldehyde groups are first aminated, and then the amine is coupled to a carrier via a linker. In the second method, sialic acid residues and/or N-acetyl-glucosamine residues are de-N-acetylated to give amine groups, and the amine groups are coupled to a carrier protein via a linker. In the third method, linkage is via galactose residues in the capsular saccharide rather than sialic acid residues, which can conveniently be achieved using galactose oxidase.

18 Claims, 8 Drawing Sheets

(56) References Cited

U.S. PATENT DOCUMENTS

| | | | |
|---|---|---|---|
| 6,960,344 B2* | 11/2005 | Marciani | 424/193.1 |
| 7,700,578 B2* | 4/2010 | Guerry et al. | 514/55 |
| 2001/0051364 A1* | 12/2001 | Michon et al. | 435/101 |
| 2003/0170267 A1* | 9/2003 | Paoletti | 424/201.1 |
| 2004/0052804 A1* | 3/2004 | Arumugham et al. | 424/184.1 |
| 2004/0142856 A1* | 7/2004 | DeFrees et al. | 514/8 |
| 2004/0213804 A1 | 10/2004 | Michon et al. | |
| 2005/0169941 A1* | 8/2005 | Lees | 424/234.1 |
| 2006/0134142 A1* | 6/2006 | Kasper et al. | 424/244.1 |
| 2006/0198819 A1* | 9/2006 | Behrens et al. | 424/85.1 |
| 2007/0110762 A1* | 5/2007 | Jessouroun et al. | 424/190.1 |
| 2007/0141084 A1* | 6/2007 | Lee et al. | 424/236.1 |
| 2008/0312137 A1* | 12/2008 | Swennen | 514/8 |
| 2009/0136547 A1* | 5/2009 | Telford et al. | 424/244.1 |

OTHER PUBLICATIONS

Bayer, Edward A et al, Analytical Biochemistry, vol. 170, pp. 271-281, 1988, Biocytin hydrazide-A selective label for sialic acids, Galactose and other sugars in glycoconjugates using Avidin-Biotin Technology.*

Wessels, MR et al, Journal of Clinical Investigation, vol. 86, pp. 1428-1433, 1990.*

Wessels, MR et al, the Journal of Biological Chemistry, vol. 266(11) Apr. 15, pp. 6714-6719, 1991, Structural determinations and immunochemical characterization of the Type V Group B Streptococcus Capsular Polysaccharide.*

Wessels, MR et al, Journal of Cinical Investigation, 1990, vol. 86, pp. 1428-1433, Immunogenicity in Animals of a Polysaccharide-Protein Conjugate Vaccine against Type III Group B Streptococcus.*

Jennings, H, the Journal of Infectious Diseases, vol. 165, Supplement 1, Epidemiology, Jun. 1992, pp. S156-S159, Further Approaches for Optimizing Polysaccharid-Protein Conjugate Vaccines for Prevention of Invasive Bacterial Disease.*

Baker, CJ et al, Infection and Immunity, Jan. 1976, vol. 13(1), pp. 284-288, Indentiication of sialic acid in polysaccharide antigens of Group B Streptococcus.*

Kasper, Dennis L et al, Immunochemical Analysis and Immunogenicity of the Type II Group B Streptococcal Capsular Polysaccharide, Journal of Cinical Investigation, vol. 72, Jul. 1983, pp. 260-269.*

Paoletti, Lawrence C et al, The Journal of Biological Chemistry, vol. 265(30) Oct. 25, 1990, pges 18278-18283, An Oligosaccharide-Tetanus toxoid Conjugate Vaccine against Type III Group B Streptococcus.*

Shen et al., "Preparation and preclinical evaluation of experimental group B streptococcus type III polysaccharide cholera toxin B subunit conjugate vaccine for intranasal immunization," Vaccine 19, 7-8, Nov. 22, 2001.

Shen et al., "Group B streptococcus capsular polysaccharide-cholera toxin B subunit conjugate vaccines prepared by different methods for intranasal immunization," Inf. Immun. 69, 297-306, Jan. 1, 2001.

* cited by examiner

FIGURE 3

| | |
|---|---|
| Ia | $[\rightarrow 4)\text{-}\beta\text{-D-Glc}p\text{-}(1\rightarrow 4)\text{-}\beta\text{-D-Gal}p\text{-}(1\rightarrow]_n$<br>$\phantom{xxxxxxxxxxxxxxx}3$<br>$\phantom{xxxxxxxxxxxxxxx}\uparrow$<br>$\phantom{xxxxxxxxxxxxxxx}1$<br>$\phantom{xxxxxxxxxx}\beta\text{-D-Glc}p\text{NAc}$<br>$\phantom{xxxxxxxxxxxxxxx}4$<br>$\phantom{xxxxxxxxxxxxxxx}\uparrow$<br>$\phantom{xxxxxxxxxxxxxxx}1$<br>$\phantom{xxxxxxxxxx}\beta\text{-D-Gal}p$<br>$\phantom{xxxxxxxxxxxxxxx}3$<br>$\phantom{xxxxxxxxxxxxxxx}\uparrow$<br>$\phantom{xxxxxxxxxxxxxxx}2$<br>$\phantom{xxxxxxxxxx}\alpha\text{-D-Neu}p\text{NAc}$ |
| Ib | $[\rightarrow 4)\text{-}\beta\text{-D-Glc}p\text{-}(1\rightarrow 4)\text{-}\beta\text{-D-Gal}p\text{-}(1\rightarrow]_n$<br>$\phantom{xxxxxxxxxxxxxxx}3$<br>$\phantom{xxxxxxxxxxxxxxx}\uparrow$<br>$\phantom{xxxxxxxxxxxxxxx}1$<br>$\phantom{xxxxxxxxxx}\beta\text{-D-Glc}p\text{NAc}$<br>$\phantom{xxxxxxxxxxxxxxx}3$<br>$\phantom{xxxxxxxxxxxxxxx}\uparrow$<br>$\phantom{xxxxxxxxxxxxxxx}1$<br>$\phantom{xxxxxxxxxx}\beta\text{-D-Gal}p$<br>$\phantom{xxxxxxxxxxxxxxx}3$<br>$\phantom{xxxxxxxxxxxxxxx}\uparrow$<br>$\phantom{xxxxxxxxxxxxxxx}2$<br>$\phantom{xxxxxxxxxx}\alpha\text{-D-Neu}p\text{NAc}$ |
| II | $[\rightarrow 4)\text{-}\beta\text{-D-Glc}p\text{NAc-}(1\rightarrow 3)\text{-}\beta\text{-D-Gal}p\text{-}(1\rightarrow 4)\text{-}\beta\text{-D-Glc}p\text{-}(1\rightarrow 3)\text{-}\beta\text{-D-Glc}p\text{-}(1\rightarrow 2)\text{-}\beta\text{-D-Gal}p\text{-}(1\rightarrow]_n$<br>$\phantom{xx}6\phantom{xxxxxxxxxxxxxxxxxxxxxxxxxxxxxxxxxxxxxxxxxxxxxxxxxxxxxxxxxxxxxxxx}3$<br>$\phantom{xx}\uparrow\phantom{xxxxxxxxxxxxxxxxxxxxxxxxxxxxxxxxxxxxxxxxxxxxxxxxxxxxxxxxxxxxxxxx}\uparrow$<br>$\phantom{xx}1\phantom{xxxxxxxxxxxxxxxxxxxxxxxxxxxxxxxxxxxxxxxxxxxxxxxxxxxxxxxxxxxxxxxx}2$<br>$\beta\text{-D-Gal}p\phantom{xxxxxxxxxxxxxxxxxxxxxxxxxxxxxxxxxxxxxxxxxxxxxxxx}\alpha\text{-D-Neu}p\text{NAc}$ |
| III | $\rightarrow 4)\text{-}\beta\text{-D-Glc}p\text{-}(1\rightarrow 6)\text{-}\beta\text{-D-Glc}p\text{NAc-}(1\rightarrow 3)\text{-}\beta\text{-D-Gal}p\text{-}(1\rightarrow$<br>$\phantom{xxxxxxxxxxxxxxxxxxxxxxx}4$<br>$\phantom{xxxxxxxxxxxxxxxxxxxxxxx}\uparrow$<br>$\phantom{xxxxxxxxxxxxxxxxxxxxxxx}1$<br>$\phantom{xxxxxxxxxxxxxxxxxx}\beta\text{-D-Gal}p$<br>$\phantom{xxxxxxxxxxxxxxxxxxxxxxx}3$<br>$\phantom{xxxxxxxxxxxxxxxxxxxxxxx}\uparrow$<br>$\phantom{xxxxxxxxxxxxxxxxxxxxxxx}2$<br>$\phantom{xxxxxxxxxxxxxxxxxx}\alpha\text{-D-Neu}p\text{NAc}$ |
| V | $\rightarrow 4)\text{-}\alpha\text{-D-Glc}p\text{-}(1\rightarrow 4)\text{-}\beta\text{-D-Gal}p\text{-}(1\rightarrow 4)\text{-}\beta\text{-D-Glc}p\text{-}(1\rightarrow$<br>$\phantom{xxxxxxx}6\phantom{xxxxxxxxxxxxxxxxx}3$<br>$\phantom{xxxxxxx}\uparrow\phantom{xxxxxxxxxxxxxxxxx}\uparrow$<br>$\phantom{xxxxxxx}1\phantom{xxxxxxxxxxxxxxxxx}1$<br>$\beta\text{-D-Glc}p\text{NAc}\phantom{xxxx}\beta\text{-D-Glc}p$<br>$\phantom{xxxxxxx}4$<br>$\phantom{xxxxxxx}\uparrow$<br>$\phantom{xxxxxxx}1$<br>$\phantom{xx}\beta\text{-D-Gal}p$<br>$\phantom{xxxxxxx}3$<br>$\phantom{xxxxxxx}\uparrow$<br>$\phantom{xxxxxxx}2$<br>$\alpha\text{-D-Neu}p\text{NAc}$ |

CONJUGATION OF STREPTOCOCCAL CAPSULAR SACCHARIDES

All documents cited herein are incorporated by reference in their entirety.

TECHNICAL FIELD

This invention is in the field of conjugating bacterial capsular saccharides to carriers in order to form glycoconjugates. The glycoconjugates are useful for immunisation.

BACKGROUND ART

The capsular saccharides of bacteria have been used for many years in vaccines against capsulated bacteria. As saccharides are T-independent antigens, however, they are poorly immunogenic. Conjugation to a carrier can convert T-independent antigens into T-dependent antigens, thereby enhancing memory responses and allowing protective immunity to develop. The most effective saccharide vaccines are therefore based on glycoconjugates, and the prototype conjugate vaccine was against *Haemophilus influenzae* type b ('Hib') [e.g. see chapter 14 of ref. 78].

Another bacterium for which conjugate vaccines have been described is *Streptococcus agalactiae*, also known as 'group B *streptococcus*', or simply as 'GBS'. Much of this work has been performed by Dennis Kasper and colleagues, and is described in documents such as references 1 to 9. The Kasper process for GBS saccharide conjugation typically involves reductive amination of a purified saccharide to a carrier protein such as tetanus toxoid (TT) or CRM197 [2]. The reductive amination involves an amine group on the side chain of an amino acid in the carrier and an aldehyde group in the saccharide. As GBS capsular saccharides do not include an aldehyde group in their natural form then this is generated before conjugation by periodate oxidation of a portion of the saccharide's sialic acid residues, as shown in FIG. 1 [2,10].

Although conjugate vaccines prepared in this manner for each of GBS serotypes Ia, Ib, II, III, and V have been shown to be safe and immunogenic in humans [11], there remains a need for further and better ways of preparing conjugates of GBS capsular saccharides.

DISCLOSURE OF THE INVENTION

The invention is based on three conjugation methods that can be used in place of the direct reductive amination disclosed in the prior art, all of which aim (a) to retain sialic acid residues in a form that is closer than the prior art to the form see in the native polysaccharide, and (b) to allow the use of a linker in the conjugation reaction, in order to improve coupling to carriers:

In the first method, reductive amination of oxidised sialic acid residue side chains is used, but the aldehyde groups are first aminated, and then the amine is coupled to a carrier via a linker. This method is illustrated in 'route A' of FIG. 2.

In the second method, sialic acid residues and/or N-acetylglucosamine residues are de-N-acetylated to give amine groups, and the amine groups are coupled to a carrier protein via a linker. This method is illustrated in 'route B' of FIG. 2.

In the third method, linkage is via galactose residues in the capsular saccharide rather than sialic acid residues. This method avoids disrupting key epitopes formed by sialic acid residues.

In a first aspect, therefore, the invention provides a process for preparing a conjugate of a *S. agalactiae* capsular saccharide and a carrier molecule, comprising the steps of: (a) oxidising a *S. agalactiae* capsular saccharide in order to introduce an aldehyde group into at least one terminal sialic acid residue in the saccharide; (b) subjecting the aldehyde group to reductive amination with ammonia or a primary amine, to give a —CH$_2$-linked amine; (c) reacting the —CH$_2$-linked amine with a bifunctional linker, to give an activated saccharide; and (d) reacting the activated saccharide with a carrier molecule, thereby giving the conjugate. The invention also provides a conjugate, wherein the conjugate comprises a *S. agalactiae* capsular saccharide moiety joined to a carrier via a linker moiety, and wherein the linker moiety is attached to a sialic acid residue in the capsular saccharide moiety.

In a second aspect, the invention provides a process for preparing a conjugate of a *S. agalactiae* capsular saccharide and a carrier molecule, comprising the steps of: (a) de-N-acetylating the capsular saccharide, to give a de-N-acetylated saccharide; (b) reacting the de-N-acetylated saccharide with a bifunctional linker, to give an activated saccharide; and (c) reacting the activated saccharide with a carrier molecule, thereby giving the conjugate. Between steps (a) and (b), the process may involve a step of partial re-N-acetylation of the saccharide.

In a third aspect, the invention provides a process for preparing a conjugate of a capsular saccharide and a carrier molecule, comprising the steps of: (a) oxidising a capsular saccharide in order to introduce an aldehyde group into at least one galactose residue in the saccharide, to give a modified galactose residue; and (b) coupling the modified galactose residue to a carrier molecule. The coupling in step (b) may be direct, or may be via a linker molecule. The invention also provides a conjugate, wherein the conjugate comprises a capsular saccharide moiety joined to a carrier via a linker moiety, and wherein the linker moiety is attached to a galactose residue in the capsular saccharide moiety. Oxidation of galactose residues is particularly useful for conjugation of *S. agalactiae* capsular saccharides, but is also suitable for use with other bacteria that have galactose-containing capsular saccharides e.g. in *Neisseria meningitidis* (serogroup W135), *Vibrio cholerae* (including O139), *Klebsiella pneumoniae* (including K21), *Escherichia coli* (including K52), *Streptococcus pneumoniae* (including type 18C), etc. This process can also be used with galactose-containing lipopolysaccharides and lipooligosaccharides. It is particularly useful where the galactose is a terminal residue of the saccharide.

The Capsular Saccharide

The invention is based on the capsular saccharide of *Streptococcus agalactiae*. The capsular polysaccharide is covalently linked to the peptidoglycan backbone of GBS, and is distinct from the group B antigen, which is another saccharide that is attached to the peptidoglycan backbone.

The GBS capsular polysaccharides are chemically related, but are antigenically very different. All GBS capsular polysaccharides share the following trisaccharide core:

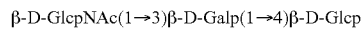

The various GBS serotypes differ by the way in which this core is modified. The difference between serotypes Ia and III, for instance, arises from the use of either the GlcNAc (Ia) or the Gal (III) in this core for linking consecutive trisaccharide cores (FIG. 4). Serotypes Ia and Ib both have a [α-D-Neup-NAc(2→3)β-D-Galp-(1→] disaccharide linked to the GlcNAc in the core, but the linkage is either 1→4 (Ia) or 1→3 (Ib).

GBS-related disease arises primarily from serotypes Ia, Ib, II, III, IV, V, VI, VII, and VIII, with over 90% being caused by five serotypes: Ia, Ib, II, III & V. The invention preferably uses a saccharide from one of these five serotypes. As shown in FIG. 3, the capsular saccharides of each of these five serotypes include: (a) a terminal N-acetyl-neuraminic acid (NeuNAc) residue (commonly referred to as sialic acid), which in all cases is linked 2→3 to a galactose residue; and (b) a N-acetyl-glucosamine residue (GlcNAc) within the trisaccharide core.

All five saccharides include galactose residues within the trisaccharide core, but serotypes Ia, Ib, II & III also contain additional galactose residues in each repeating unit, with the serotype II saccharide containing three galactose residues per repeating unit. In the third aspect of the invention, the galactose residues involved in the conjugation reactions may be a residue in the trisaccharide core or a residue outside the trisaccharide core. Where a single saccharide molecule is linked to multiple carrier molecules, it is preferred that the linkages involve the same-positioned galactose in the various linked repeating units, but it is also possible to link to differently-positioned galactose residues in different repeating units.

Saccharides used according to the invention may be in their native form, or may have been modified. For example, the saccharide may be shorter than the native capsular saccharide, or may be chemically modified.

Thus the saccharide used according to the invention may be a substantially full-length capsular polysaccharide, as found in nature, or it may be shorter than the natural length. Full-length polysaccharides may be depolymerised to give shorter fragments for use with the invention e.g. by hydrolysis in mild acid, by heating, by sizing chromatography, etc. Chain length has been reported to affect immunogenicity of GBS saccharides in rabbits [4]

Depolymerisation of the serotype III capsular saccharide by endo-β-galactosidase has been reported [refs. 1 & 4-6], including using the depolymerised material to form conjugates with a tetanus toxoid carrier. Ozonolysis of capsular polysaccharides from GBS serotypes II, III and VIII has also been used for depolymerisation [12]. It is preferred to use saccharides with MW>30 kDa, and substantially full-length capsular polysaccharides can be used. For serotype Ia, it is preferred to use polysaccharides with a MW up to ~145 kDa. For serotype Ib, it is preferred to use polysaccharides with a MW up to ~50 kDa. For serotype III, it is preferred to use polysaccharides with a MW up to ~50 kDa. These molecular masses can be measured by gel filtration relative to dextran standards, such as those available from Polymer Standard Service [13].

The saccharide may be chemically modified relative to the capsular saccharide as found in nature. For example, the saccharide may be de-O-acetylated (partially or fully), de-N-acetylated (partially or fully), N-propionated (partially or fully), etc. De-acetylation may occur before, during or after conjugation, but preferably occurs before conjugation. Depending on the particular saccharide, de-acetylation may or may not affect immunogenicity e.g. the NeisVac-C™ vaccine uses a de-O-acetylated saccharide, whereas Menjugate™ is acetylated, but both vaccines are effective. The relevance of O-acetylation on GBS saccharides in various serotypes is discussed in reference 14, and it is preferred to retain O-acetylation of sialic acid residues at positions 7, 8 and/or 9 before during and after conjugation e.g. by protection/de-protection, by re-acetylation, etc. The effect of de-acetylation etc. can be assessed by routine assays.

Capsular saccharides can be purified by known techniques, as described in the references herein. A typical process involves base extraction, centrifugation, filtration, RNase/DNase treatment, protease treatment, concentration, size exclusion chromatography, ultrafiltration, anion exchange chromatography, and further ultrafiltration. Treatment of GBS cells with the enzyme mutanolysin, which cleaves the bacterial cell wall to free the cell wall components, is also useful.

As an alternative, the purification process described in reference 15 can be used. This involves base extraction, ethanol/$CaCl_2$ treatment, CTAB precipitation, and re-solubilisation.

The invention is not limited to saccharides purified from natural sources, however, and the saccharides may be obtained by other methods, such as total or partial synthesis.

The Carrier

The invention involves the use of carrier molecules, which are typically proteins. In general, covalent conjugation of saccharides to carriers enhances the immunogenicity of saccharides as it converts them from T-independent antigens to T-dependent antigens, thus allowing priming for immunological memory. Conjugation is particularly useful for paediatric vaccines [e.g. ref. 16] and is a well known technique [e.g. reviewed in refs. 17 to 25].

Preferred carrier proteins are bacterial toxins or toxoids, such as diphtheria toxoid or tetanus toxoid. The CRM197 mutant of diphtheria toxin [26-28] is a particularly preferred carrier for, as is a diphtheria toxoid. Other suitable carrier proteins include the N. meningitidis outer membrane protein [29], synthetic peptides [30,31], heat shock proteins [32,33], pertussis proteins [34,35], cytokines [36], lymphokines [36], hormones [36], growth factors [36], human serum albumin (preferably recombinant), artificial proteins comprising multiple human $CD4^+$ T cell epitopes from various pathogen-derived antigens [37] such as N19 [38], protein D from H. influenzae [39,40], pneumococcal surface protein PspA [41], pneumolysin [42], iron-uptake proteins [43], toxin A or B from C. difficile [44], a GBS protein (see below; particularly GBS67) [195], etc.

Attachment to the carrier is preferably via a —$NH_2$ group e.g. in the side chain of a lysine residue in a carrier protein, or of an arginine residue. Where a saccharide has a free aldehyde group then this can react with an amine in the carrier to form a conjugate by reductive amination. The third aspect of the invention may be based on reductive amination involving an oxidised galactose in the saccharide (from which an aldehyde is formed) and an amine in the carrier or in the linker. Attachment may also be via a —SH group e.g. in the side chain of a cysteine residue.

It is possible to use more than one carrier protein e.g. to reduce the risk of carrier suppression. Thus different carrier proteins can be used for different GBS serotypes e.g. serotype Ia saccharides might be conjugated to CRM197 while serotype Ib saccharides might be conjugated to tetanus toxoid. It is also possible to use more than one carrier protein for a particular saccharide antigen e.g. serotype III saccharides might be in two groups, with some conjugated to CRM197 and others conjugated to tetanus toxoid. In general, however, it is preferred to use the same carrier protein for all saccharides.

A single carrier protein might carry more than one saccharide antigen [45,46]. For example, a single carrier protein might have conjugated to it saccharides from serotypes Ia and Ib. To achieve this goal, different saccharides can be mixed prior to the conjugation reaction. In general, however, it is preferred to have separate conjugates for each serogroup, with the different saccharides being mixed after conjugation. The separate conjugates may be based on the same carrier.

Conjugates with a saccharide:protein ratio (w/w) of between 1:5 (i.e. excess protein) and 5:1 (i.e. excess saccharide) are preferred. Ratios between 1:2 and 5:1 are preferred, as are ratios between 1:1.25 and 1:2.5. Ratios between 1:1 and 4:1 are also preferred. With longer saccharide chains, a weight excess of saccharide is typical. As shown in the examples, a weight ratio between 1:1 and 4:1, and particularly 1:1 and 3:1, can readily be achieved. In general, the invention provides a conjugate, wherein the conjugate comprises a *S. agalactiae* capsular saccharide moiety joined to a carrier, wherein the weight ratio of saccharide:carrier is at least 2:1.

Compositions may include a small amount of free carrier [47]. When a given carrier protein is present in both free and conjugated form in a composition of the invention, the unconjugated form is preferably no more than 5% of the total amount of the carrier protein in the composition as a whole, and more preferably present at less than 2% by weight.

After conjugation, free and conjugated saccharides can be separated. There are many suitable methods, including hydrophobic chromatography, tangential ultrafiltration, diafiltration etc. [see also refs. 48 & 49, etc.].

Where the composition of the invention includes a depolymerised oligosaccharide, it is preferred that depolymerisation precedes conjugation.

Introduction of Aldehyde Groups

The first aspect of the invention involves oxidation of sialic acid to form an aldehyde, and the third aspect involves oxidation of galactose to form an aldehyde. The aldehyde can then be used for reactions such as reductive amination.

Oxidation of hydroxyls to give aldehydes can be achieved chemically or enzymatically. These reactions will typically take place in aqueous conditions.

Methods for oxidation of sialic acids in GBS saccharides in order to introduce aldehyde groups for reductive amination are known in the art [e.g. ref. 50]. Typical reactions to produce aldehydes in sialic acids include the use of periodate salts, and particularly meta-periodates (e.g. sodium or potassium meta-periodate e.g. $NaIO_4$), to oxidise vicinal hydroxides [10]. Periodate oxidation has been reported for at least serogroups II [3,50], III [2] and V [50]. Other oxidation conditions can be used e.g. use of osmium tetroxide, etc.

In the third aspect of the invention, the —OH that is oxidised is preferably the primary —OH (i.e. not the secondary or anomeric —OH groups), which is attached to C-6. Thus it is preferred to convert galactose into galactohexodialose. This can conveniently be achieved using a galactose oxidase enzyme, from any suitable source (e.g. from *Fusarium* fungi, or *Dactylium dendroides*). The enzyme can be used in recombinant form, or purified from its native source. The galactose oxidase enzyme has EC number 1.1.3.9, and is also known as D-Galactose:oxygen 6-oxidoreductase. The enzyme uses a copper ion cofactor and can be inhibited by cyanide, diethyldithiocarbamate, azide and hydroxylamine, so use of these reagents prior to oxidation is preferably avoided. The pH optimum for the *D. dendroides* is around neutral, which is thus the preferred pH for oxidation. A product of the enzymatic reaction is $H_2O_2$ (reduced oxygen), and the concentration of this product can be controlled e.g. if its presence is damaging to the saccharide.

For both sialic acid and galactose, therefore, the preferred oxidation reactions involve the terminal carbon atoms in the monosaccharides i.e. the highest-numbered carbons by standard nomenclature.

The proportion of monosaccharide subunits in a saccharide chain that are converted to include an aldehyde group can be controlled by varying reaction conditions. For example, reference 50 reports that controlled periodate oxidation of serotype II GBS polysaccharide resulted in the modification of 7% of sialic acid residues as determined by gas chromatography-mass spectrometry analysis, with a higher percentage being seen for serotype V GBS polysaccharide. Reference 2 reports 25% conversion for serotype III. Preliminary studies of reaction conditions (e.g. time, temperature, concentrations, etc.) can be performed to find optimum conditions for any desired end result.

In general, it is typical to introduce aldehyde groups into between 5% and 50% (e.g. 10-40%, preferably between 15%-30%; or between 5% and 20%) of the total sialic acid or galactose monosaccharide units within a saccharide. Higher percentages lead to saccharides that are more difficult to handle, without any corresponding increase in immunogenicity, Reductive Amination In the first aspect of the invention, reductive amination of the new aldehyde group is used to give a group for attachment of the linker. Reductive amination can also be used in the third aspect of the invention after the aldehyde group has been produced, either to attach a linker or for direct linkage to a carrier. Reductive amination is a standard technique in organic chemistry, and has been used extensively in the production of conjugates of capsular saccharides for vaccine use.

In the first aspect, the reductive amination involves either ammonia or a primary amine ($NH_2R$). This can conveniently be achieved by using an ammonium salt (e.g. ammonium chloride) in combination with an appropriate reducing agent (e.g. cyanoborohydrides, such as sodium cyanoborohydride $NaBH_3CN$; borane-pyridine; sodium triacetoxyborohydride; borohydride exchange resin; etc.). The result of reductive amination is that C-8 in the sialic acid carries —NHR rather than =O. This group can then be used for attachment of a bifunctional linker for conjugation.

In the third aspect, the oxidised galactose has an aldehyde group on C-6. This group can be coupled to a bifunctional linker by reductive amination in the same way as described above i.e. involving ammonia or a primary amine. As an alternative, reductive amination can be used to link the aldehyde to a carrier directly, without use of a linker, by utilising an amine group on the carrier.

Reductive amination will generally be carried out in a polar protic solvent, such as water or alcohol.

Bifunctional Linker

The first and second aspects of the invention (and, optionally, the third aspect) involve the use of a bifunctional linker. A bifunctional linker is used to provide a first group for coupling to an amine group in the modified capsular saccharide and a second group for coupling to the carrier (typically for coupling to an amine in the carrier).

The first group in the bifunctional linker is thus able to react with the amine group (—NHR) on the modified sialic acid (or galactose) residue. This reaction will typically involve an electrophilic substitution of the amine's hydrogen. The second group in the bifunctional linker is able to react with the amine group on the carrier. This reaction will again typically involve an electrophilic substitution of the amine. The invention can use both heterobifunctional linkers and homobifunctional linkers.

Where the reactions with both the saccharide and the carrier involve amines then it is preferred to use a bifunctional linker of the formula X-L-X, where: the two X groups are the same as each other and can react with the amines; and where L is a linking moiety in the linker. A preferred X group is N-oxysuccinimide. L preferably has formula -L'-$L^2$-L'-, where L¹ is carbonyl. Preferred L² groups are straight chain alkyls with 1 to 10 carbon atoms (e.g. $C_1$, $C_2$, $C_3$, $C_4$, $C_5$, $C_6$, $C_7$, $C_8$, $C_9$, $C_{10}$) e.g. —$(CH_2)_4$—. A preferred linker is thus adipic acid N-hydroxysuccinimide diester (SIDEA):

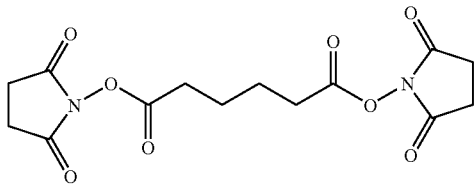 [SMILES: O=C(CCCCC(=O)ON1C(=O)CCC1=O)ON1C(=O)CCC1=O]

Other X groups are those which form esters when combined with HO-L-OH, such as norborane, p-nitrobenzoic acid, and sulfo-N-hydroxysuccinimide.

Further bifunctional linkers reactive with amines for use with the invention include acryloyl halides (e.g. chloride) [54], haloacylhalides [55], disuccinimidyl glutarate, disuccinimidyl suberate, ethylene glycol bis[succinimidylsuccinate], etc.

The linker will generally be added in molar excess to modified saccharide.

The linker/saccharide reaction will generally take place in an aprotic solvent (e.g. DMSO, ethanol acetate, etc.), as the linkers are typically insoluble in water. Where water-soluble linkers are used, however, then a wider range of solvents is available, including protic solvents such as water. Suitable linkers include sulphonated forms, such as sulphonated SIDEA:

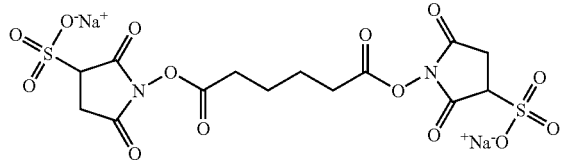

De-N-acetylation and re-N-acetylation

The sialic acid residues in GBS capsular saccharides are N-acetylated, as are the glucosamine residues within the trisaccharide core. Whereas the first aspect of the invention introduces amine groups in at C-8 of the sialic acid via an aldehyde intermediate, the second aspect of the invention uses amine groups produced by de-N-acetylation of the sialic acid and/or N-acetyl-glucosamine residues. The reaction schemes for amines produced in this way are generally the same as described for the first aspect of the invention.

De-N-acetylation of GBS saccharides can conveniently be achieved by treating the saccharide with a base. As GBS saccharides can be purified by a process involving base extraction [51] then de-N-acetylation may be a side-reaction during purification.

Because N-acetyl groups may be part of important epitopes in GBS saccharides, complete de-N-acetylation may not be desirable, but this process is difficult to control. If the extent of de-N-acetylation is greater than desired, therefore, the invention may involve a step of controlled re-N-acetylation. Re-N-acetylation can conveniently be performed using a reagent such as acetic anhydride ($CH_3CO)_2O$ e.g. in 5% ammonium bicarbonate [52]. Rather than use re-N-acetylation, however, the inventors have found that base extraction of the saccharide from bacteria can, if performed quickly enough without prolonged storage of the saccharide, give a saccharide with less than 25% de-N-acetylation.

The result of de-N-acetylation and optional re-N-acetylation is a saccharide in which at least 1 sialic acid residue or glucosamine is de-N-acetylated. Typically, at least 60% of the sialic acid residues and glucosamine residues in the GBS saccharide are N-acetylated e.g. ≧70%, ≧75%, ≧80%, ≧85%, ≧90%, etc. The remaining de-N-acetylated groups (i.e. —$NH_2$ groups) can be used for conjugation in the same way as described for the first aspect of the invention, except that the —NH— in the final conjugate will be derived from the original saccharide rather than being added during the conjugation reaction.

These de- and re-acetylation reactions can be performed in aqueous conditions.

In embodiments of the first and third aspects of the invention where the aldehyde is reductively aminated, it is preferred that the saccharide is substantially totally re-N-acetylated prior to the reductive amination (preferably prior to oxidation of galactose in the third aspect), in order to avoid the presence of free amine groups on sialic acids that would otherwise offer alternative linking groups to the aminated aldehyde.

The Conjugate

Conjugates of the invention are formed by mixing the modified GBS saccharide with the carrier under suitable reaction conditions. In general, two types of conjugate can be made, as shown in FIG. 5: (a) a conjugate where an individual saccharide is attached to a single carrier e.g. through its reducing terminus; and (b) a conjugate where an individual saccharide is attached to multiple carriers e.g. because several monosaccharide subunits are reactive. In both situations a single carrier protein can link to multiple saccharide molecules because it can have multiple exposed lysine side chains.

Conjugates of type (b) are more typical in the present invention, because the modified sialic acid or galactose residues of the invention occur at multiple sites along a single saccharide [50]. In preferred conjugates of the invention, therefore, a single saccharide molecule is coupled on average to more than one carrier molecule.

In the first and third methods of the invention, where oxidised saccharides are used for conjugation, the number of carrier molecules attached to a saccharide will depend on the number of free aldehyde groups that are present. As mentioned above, it is preferred that 5-50% of sialic acid (first method) or galactose (third method) residues in the saccharide are oxidised.

In the first and second aspects of the invention (and optionally in the third) the conjugates will include a linker moiety. This linker moiety originates neither in the saccharide nor the carrier, but is a third molecule used during conjugate preparation, and can readily be distinguished from both the saccharide and carrier protein in a final conjugate product.

The linker moiety may include atoms such as carbon, hydrogen, oxygen and/or nitrogen. Linkers that comprise carbon and hydrogen are preferred, and linkers that further comprise oxygen and/or nitrogen are also preferred. Linkers that include nitrogen atoms may include a carbon atom bonded to a nitrogen atom, which in turn is bonded to a second carbon atom (—C—N—C—). Linkers that include an oxygen atom preferably include it as part of a carbonyl group. Linker moieties with a molecular weight of between 30-500 Da are preferred. Linkers containing two carbonyl groups are preferred.

A particularly preferred linker moiety is —NH—C(O)—$(CH_2)_n$—C(O)—, wherein n is 1, 2, 3, 4, 5, 6, 7, 8, 9 or 10. The value of n is preferably 4. The terminal —NH— in this linker is preferably attached to a carbon atom from the saccharide moiety. The terminal —C(O)— is preferably attached to a nitrogen atom in an amino acid side chain in the carrier. The preferred linker moiety can conveniently be introduced by a process involving: reductive amination of an aldehyde in an oxidised sialic acid; reaction of the resulting —NH$_2$ group with a bifunctional linker that is a diester (e.g. a disuccinimidyl ester) of a dioic acid (e.g. of adipic acid, HOOC—(CH$_2$)$_4$—COOH); and reductive amination of the product (see FIG. 6).

Other chemistries that can be used to attach a linker to a terminal —NH$_2$ in a saccharide, which may have been introduced (as in the first aspect of the invention) or may be part of a de-N-acetylated monosaccharide residue (as in the second aspect of the invention), include:

acryloylation (e.g. by reaction with acryloyl chloride), followed by Michael-type addition to either the ϵ-NH$_2$ of an amino acid side chain or to a —SH of a cysteine side chain [54]. The resulting linker is —NH—C(O)—(CH$_2$)$_2$— (propionamido), as shown in FIG. 8, or —C(O)—(CH$_2$)$_2$— if an existing —NH$_2$ takes part in the reaction.

reaction with a haloacylhalide, followed by reaction with the ϵ-NH$_2$ of an amino acid side chain or to a —SH of a cysteine side chain [55]. The linker is —NH—C(O)—CH$_2$— (as shown in FIG. 9) or —C(O)—CH$_2$—, depending on whether an existing or added —NH$_2$ takes part in the reaction.

Another preferred linker moiety is —C(O)—(CH$_2$)$_n$—C(O)—, wherein n is 1, 2, 3, 4, 5, 6, 7, 8, 9 or 10. The value of n is preferably 4. One terminal —C(O)— in this linker is preferably attached to a nitrogen carbon atom from the saccharide moiety, and the other terminal —C(O)— is preferably attached to a nitrogen atom in an amino acid side chain in the carrier. The preferred linker moiety can conveniently be introduced by a process involving: reaction of a —NH$_2$ group in a de-N-acetylated monosaccharide unit with a bifunctional linker that is a diester (e.g. a disuccinimidyl ester) of a dioic acid (e.g. of adipic acid, HOOC—(CH$_2$)$_4$—COOH); and reductive amination of the product (FIG. 7). Other options include conjugating via hydroxyl groups in the saccharide. Hydroxyls can be activated (e.g. by CNBr or CDAP) and then subjected to conjugation.

Combinations of Conjugates and Other Antigens

As well as providing individual conjugates as described above, the invention provides a composition comprising a conjugate of the invention and one or more further antigens.

The further antigen(s) may comprise further conjugates of the invention, and so the invention provides a composition comprising more than one conjugate of the invention. The further antigen(s) may be GBS saccharide conjugates prepared by methods other than those of the invention, and so the invention provides a composition comprising a first GBS saccharide conjugate and a second GBS saccharide conjugate, wherein the first conjugate is a conjugate of the invention and the second conjugate is not a conjugate of the invention.

The different GBS conjugates may include different types of conjugate from the same GBS serotype and/or conjugates from different GBS serotypes. For example, the invention provides a composition comprising conjugates from two or three of serotypes Ia, Ib and III. The composition will be produced by preparing separate conjugates (e.g. a different conjugate for each serotype) and then combining the conjugates.

The further antigen(s) may comprise GBS amino acid sequences, as set out below.

The further antigen(s) may comprise antigens from non-GBS pathogens. Thus the compositions of the invention may further comprise one or more non-GBS antigens, including additional bacterial, viral or parasitic antigens. These may be selected from the following:

a protein antigen from *N. meningitidis* serogroup B, such as those in refs. 56 to 62, with protein '287' (see below) and derivatives (e.g. 'ΔG287') being particularly preferred.

an outer-membrane vesicle (OMV) preparation from *N. meningitidis* serogroup B, such as those disclosed in refs. 63, 64, 65, 66 etc.

a saccharide antigen from *N. meningitidis* serogroup A, C, W135 and/or Y, such as the oligosaccharide disclosed in ref. 67 from serogroup C or the oligosaccharides of ref. 68.

a saccharide antigen from *Streptococcus pneumoniae* [e.g. refs. 69-71; chapters 22 & 23 of ref. 78].

an antigen from hepatitis A virus, such as inactivated virus [e.g. 72, 73; chapter 15 of ref. 78].

an antigen from hepatitis B virus, such as the surface and/or core antigens [e.g. 73,74; chapter 16 of ref. 78].

an antigen from hepatitis C virus [e.g. 75].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 76 & 77; chapter 21 of ref. 78].

a diphtheria antigen, such as a diphtheria toxoid [e.g. chapter 13 of ref. 78].

a tetanus antigen, such as a tetanus toxoid [e.g. chapter 27 of ref. 78].

a saccharide antigen from *Haemophilus influenzae* B [e.g. chapter 14 of ref. 78]

an antigen from *N. gonorrhoeae* [e.g. 56, 57, 58].

an antigen from *Chlamydia pneumoniae* [e.g. 79, 80, 81, 82, 83, 84, 85].

an antigen from *Chlamydia trachomatis* [e.g. 86].

an antigen from *Porphyromonas gingivalis* [e.g. 87].

polio antigen(s) [e.g. 88, 89; chapter 24 of ref. 78] such as IPV.

rabies antigen(s) [e.g. 90] such as lyophilised inactivated virus [e.g. 91, RabAvert™].

measles, mumps and/or rubella antigens [e.g. chapters 19, 20 and 26 of ref. 78].

influenza antigen(s) [e.g. chapters 17 & 18 of ref. 78], such as the haemagglutinin and/or neuraminidase surface proteins.

an antigen from *Moraxella catarrhalis* [e.g. 92].

an antigen from *Streptococcus pyogenes* (group A *streptococcus*) [e.g. 93, 94, 95].

an antigen from *Staphylococcus aureus* [e.g. 96].

Where a saccharide or carbohydrate antigen is used, it is preferably conjugated to a carrier in order to enhance immunogenicity. Conjugation of *H. influenzae* B, meningococcal and pneumococcal saccharide antigens is well known.

Toxic protein antigens may be detoxified where necessary (e.g. detoxification of pertussis toxin by chemical and/or genetic means [77]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens may be adsorbed to an aluminium salt.

One type of preferred composition includes further antigens from sexually-transmitted pathogens, such as: herpesvirus; *N. gonorrhoeae*; papillomavirus; *C. tachomatis*; etc. Another type of preferred composition includes further antigens that affect the elderly and/or the immunocompromised, and so the GBS antigens of the invention can be combined with one or more antigens from the following non-GBS pathogens: influenza virus, *Enterococcus faecalis, Staphylococcus aureus, Staphylococcus epidermis, Pseudomonas aeruginosa, Legionella pneumophila, Listeria monocytogenes, Neisseria meningitidis,* and parainfluenza virus.

Antigens in the composition will typically be present at a concentration of at least 1 μg/ml each. In general, the concentration of any given antigen will be sufficient to elicit an immune response against that antigen.

As an alternative to using proteins antigens in the composition of the invention, nucleic acid encoding the antigen may be used [e.g. refs. 97 to 105]. Protein components of the compositions of the invention may thus be replaced by nucleic acid (preferably DNA e.g. in the form of a plasmid) that encodes the protein.

In practical terms, there may be an upper limit to the number of antigens included in compositions of the invention. The number of antigens (including GBS antigens) in a composition of the invention may be less than 20, less than 19, less than 18, less than 17, less than 16, less than 15, less than 14, less than 13, less than 12, less than 11, less than 10, less than 9, less than 8, less than 7, less than 6, less than 5, less than 4, or less than 3. The number of GBS antigens in a composition of the invention may be less than 6, less than 5, or less than 4.

Pharmaceutical Compositions and Methods

The invention provides a pharmaceutical composition comprising (a) a conjugate of the invention and (b) a pharmaceutically acceptable carrier. Typical 'pharmaceutically acceptable carriers' include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose [106], trehalose [107], lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in reference 108.

Compositions of the invention may be in aqueous form (i.e. solutions or suspensions) or in a dried form (e.g. lyophilised). If a dried vaccine is used then it will be reconstituted into a liquid medium prior to injection. Lyophilisation of conjugate vaccines is known in the art e.g. the Menjugate™ product is presented in lyophilised form, whereas NeisVac-C™ and Meningitec™ are presented in aqueous form. To stabilise conjugates during lyophilisation, it may be preferred to include a sugar alcohol (e.g. mannitol) or a disaccharide (e.g. sucrose or trehalose) e.g. at between 1 mg/ml and 30 mg/ml (e.g. about 25 mg/ml) in the composition.

Compositions may be presented in vials, or they may be presented in ready-filled syringes. The syringes may be supplied with or without needles. A syringe will include a single dose of the composition, whereas a vial may include a single dose or multiple doses.

Aqueous compositions of the invention are also suitable for reconstituting other vaccines from a lyophilised form. Where a composition of the invention is to be used for such extemporaneous reconstitution, the invention provides a kit, which may comprise two vials, or may comprise one ready-filled syringe and one vial, with the contents of the syringe being used to reactivate the contents of the vial prior to injection.

Compositions of the invention may be packaged in unit dose form or in multiple dose form. For multiple dose forms, vials are preferred to pre-filled syringes. Effective dosage volumes can be routinely established, but a typical human dose of the composition has a volume of 0.5 ml e.g. for intramuscular injection.

The pH of the composition is preferably between 6 and 8, preferably about 7. Stable pH may be maintained by the use of a buffer. If a composition comprises an aluminium hydroxide salt, it is preferred to use a histidine buffer [109]. The composition may be sterile and/or pyrogen-free. Compositions of the invention may be isotonic with respect to humans.

Compositions of the invention are immunogenic, and are more preferably vaccine compositions. Vaccines according to the invention may either be prophylactic (i.e. to prevent infection) or therapeutic (i.e. to treat infection), but will typically be prophylactic. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Within each dose, the quantity of an individual saccharide antigen will generally be between 1-50 μg (measured as mass of saccharide) e.g. about 1 μg, about 2.5 μg, about 4 μg, about 5 μg, or about 10 μg.

GBS affects various areas of the body and so the compositions of the invention may be prepared in various forms. For example, the compositions may be prepared as injectables, either as liquid solutions or suspensions. The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 110 & 111]. Success with nasal administration of pneumococcal saccharides [112, 113], Hib saccharides [114], MenC saccharides [115], and mixtures of Hib and MenC saccharide conjugates [116] has been reported.

Compositions of the invention may include an antimicrobial, particularly when packaged in multiple dose format.

Compositions of the invention may comprise detergent e.g. a Tween (polysorbate), such as Tween 80. Detergents are generally present at low levels e.g. <0.01%.

Compositions of the invention may include sodium salts (e.g. sodium chloride) to give tonicity. A concentration of 10±2 mg/ml NaCl is typical.

Compositions of the invention will generally include a buffer. A phosphate buffer is typical.

Compositions of the invention will generally be administered in conjunction with other immunoregulatory agents. In particular, compositions will usually include one or more adjuvants. Such adjuvants include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 117], or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt [118].

Aluminum salts may be included in vaccines of the invention such that the dose of $Al^{3+}$ is between 0.2 and 1.0 mg per dose.

A typical aluminium phosphate adjuvant is amorphous aluminium hydroxyphosphate with $PO_4/Al$ molar ratio between 0.84 and 0.92, included at 0.6 mg $Al^{3+}$/ml. Adsorption with a low dose of aluminium phosphate may be used e.g. between 50 and 100 μg $Al^{3+}$ per conjugate per dose. Where an aluminium phosphate it used and it is desired not to adsorb an antigen to the adjuvant, this is favoured by including free phosphate ions in solution (e.g. by the use of a phosphate buffer).

B. Oil Emulsions

Oil emulsion compositions suitable for use as adjuvants in the invention include squalene-water emulsions, such as MF59 (5% Squalene, 0.5% Tween 80, and 0.5% Span 85, formulated into submicron particles using a microfluidizer) [Chapter 10 of ref. 117; see also refs. 119-121]. MF59 is used as the adjuvant in the FLUAD™ influenza virus trivalent subunit vaccine.

Particularly preferred adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80 (polyoxyelthylenesorbitan monooleate), and/or 0.25-1.0% Span 85 (sorbitan trioleate), and, optionally, N-acetylmuramyl-L-alanyl-D-isogluatminyl-L-alanine-2-(1'-2'-dipalmitoyl-sn-glycero-3-hydroxyphosphosphoryloxy)-ethylamine (MTP-PE). Submicron oil-in-water emulsions, methods of making the same and immunostimulating agents, such as muramyl peptides, for use in the compositions, are described in detail in references 119 & 122-123. Complete Freund's adjuvant (CFA) and incomplete Freund's adjuvant (IFA) may also be used as adjuvants in the invention.

C. Saponin Formulations [Chapter 22 of Ref. 117]

Saponin formulations may also be used as adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 124. Saponin formulations may also comprise a sterol, such as cholesterol [125].

Combinations of saponins and cholesterols can be used to form unique particles called immunostimulating complexes (ISCOMs) [chapter 23 of ref. 117]. ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in refs. 125-127. Optionally, the ISCOMS may be devoid of additional detergent(s) [128].

A review of the development of saponin based adjuvants can be found in refs. 129 & 130.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 131-136. Virosomes are discussed further in, for example, ref. 137

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof. Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 138. Such "small particles" of 3dMPL are small enough to be sterile filtered through a 0.22 μm membrane [138]. Other non-toxic LPS derivatives include monophosphoryl lipid A mimics, such as aminoalkyl glucosaminide phosphate derivatives e.g. RC-529 [139,140].

Lipid A derivatives include derivatives of lipid A from *Escherichia coli* such as OM-174. OM-174 is described for example in refs. 141 & 142.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 143, 144 and 145 disclose possible analog substitutions e.g. replacement of guanosine with 2'-deoxy-7-deazaguanosine. The adjuvant effect of CpG oligonucleotides is further discussed in refs. 146-151.

The CpG sequence may be directed to TLR9, such as the motif GTCGTT or TTCGTT [152]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 153-155. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 152 & 156-158.

Bacterial ADP-ribosylating toxins and detoxified derivatives thereof may be used as adjuvants in the invention. Preferably, the protein is derived from E. coli (E. coli heat labile enterotoxin "LT"), cholera ("CT"), or pertussis ("PT"). The use of detoxified ADP-ribosylating toxins as mucosal adjuvants is described in ref. 159 and as parenteral adjuvants in ref. 160. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 161-168. Numerical reference for amino acid substitutions is preferably based on the alignments of the A and B subunits of ADP-ribosylating toxins set forth in ref. 169, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [170], etc.) [171], interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [172] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [173].

H. Microparticles

Microparticles may also be used as adjuvants in the invention. Microparticles (i.e. a particle of ~100 nm to ~150 μm in diameter, more preferably 200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref. 117)

Examples of liposome formulations suitable for use as adjuvants are described in refs. 174-176.

J. Polyoxyethylene Ether and Polyoxyethylene Ester Formulations

Adjuvants suitable for use in the invention include polyoxyethylene ethers and polyoxyethylene esters [177]. Such formulations further include polyoxyethylene sorbitan ester surfactants in combination with an octoxynol [178] as well as polyoxyethylene alkyl ethers or ester surfactants in combination with at least one additional non-ionic surfactant such as an octoxynol [179]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 180 and 181.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds

Examples of imidazoquinolone compounds suitable for use adjuvants in the invention include Imiquamod and its homologues (e.g. "Resiquimod 3M"), described further in refs. 182 and 183.

N. Thiosemicarbazone Compounds

Examples of thiosemicarbazone compounds, as well as methods of formulating, manufacturing, and screening for compounds all suitable for use as adjuvants in the invention include those described in ref. 184. The thiosemicarbazones are particularly effective in the stimulation of human peripheral blood mononuclear cells for the production of cytokines, such as TNF-α.

O. Tryptanthrin Compounds

Examples of tryptanthrin compounds, as well as methods of formulating, manufacturing, and screening for compounds all suitable for use as adjuvants in the invention include those described in ref. 185. The tryptanthrin compounds are particularly effective in the stimulation of human peripheral blood mononuclear cells for the production of cytokines, such as TNF-α.

The invention may also comprise combinations of aspects of one or more of the adjuvants identified above. For example, the following combinations may be used as adjuvant compositions in the invention: (1) a saponin and an oil-in-water emulsion [186]; (2) a saponin (e.g. QS21)+a non-toxic LPS derivative (e.g. 3dMPL) [187]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [188]; (5) combinations of 3dMPL with, for example, QS21 and/or oil-in-water emulsions [189]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 117.

The use of aluminium salt adjuvants is particularly preferred, and antigens are generally adsorbed to such salts. The Menjugate™ and NeisVac™ conjugates use a hydroxide adjuvant, whereas Meningitec™ uses a phosphate adjuvant. It is possible in compositions of the invention to adsorb some antigens to an aluminium hydroxide but to have other antigens in association with an aluminium phosphate. In general, however, it is preferred to use only a single salt e.g. a hydroxide or a phosphate, but not both. Not all conjugates need to be adsorbed i.e. some or all can be free in solution.

Methods of Treatment

The invention also provides a method for raising an immune response in a mammal, comprising administering a pharmaceutical composition of the invention to the mammal. The immune response is preferably protective and preferably involves antibodies. The method may raise a booster response.

The mammal is preferably a human. Where the vaccine is for prophylactic use, the human is preferably a child (e.g. a toddler or infant) or a teenager; where the vaccine is for therapeutic use, the human is preferably an adult. A vaccine intended for children may also be administered to adults e.g. to assess safety, dosage, immunogenicity, etc. A preferred class of humans for treatment are females of child-bearing age (e.g. teenagers and above). Another preferred class is pregnant females.

The invention also provides a composition of the invention for use as a medicament. The medicament is preferably able to raise an immune response in a mammal (i.e. it is an immunogenic composition) and is more preferably a vaccine.

The invention also provides the use of a conjugate of the invention in the manufacture of a medicament for raising an immune response in a mammal.

These uses and methods are preferably for the prevention and/or treatment of a disease caused by *S. agalactiae* e.g. neonatal sepsis or bacteremia, neonatal pneumonia, neonatal meningitis, endometritis, osteomyelitis, septic arthritis, etc.

The subject in which disease is prevented may not be the same as the subject that receives the conjugate of the invention. For instance, a conjugate may be administered to a female (before or during pregnancy) in order to protect offspring (so-called 'maternal immunisation' [190-192]).

One way of checking efficacy of therapeutic treatment involves monitoring GBS infection after administration of the composition of the invention. One way of checking efficacy of prophylactic treatment involves monitoring immune responses against the GBS antigens after administration of the composition.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

GBS Protein Antigens

As mentioned above, GBS proteins can be included in compositions of the invention. These may be used as carrier proteins for conjugates of the invention, carrier proteins for other conjugates, or as unconjugated protein antigens.

GBS protein antigens for use with the invention include those disclosed in references 93 and 193-195. Five preferred GBS protein antigens for use with the invention are known as: GBS67; GBS80; GBS104; GBS276; and GBS322 [see ref. 93]. Further details of these five antigens are given below.

The full-length sequences for these five GBS proteins are SEQ ID NOs 1 to 5 herein. Compositions of the invention may thus include (a) a polypeptide comprising an amino acid sequence selected from SEQ ID NOs 1 to 5, and/or (b) a polypeptide comprising (i) an amino acid sequence that has sequence identity to one or more of SEQ ID NOs 1 to 5 and/or (ii) a fragment of SEQ ID NOs 1 to 5.

Depending on the particular SEQ ID NO, the degree of sequence identity in (i) is preferably greater than 50% (e.g. 60%, 70%, 75%, 80%, 85%, 90%, 91%, 92%, 93%, 94%, 95%, 96%, 97%, 98%, 99% or more). These polypeptides include homologs, orthologs, allelic variants and functional mutants. Typically, 50% identity or more between two polypeptide sequences is considered to be an indication of functional equivalence. Identity between polypeptides is preferably determined by the Smith-Waterman homology search algorithm as implemented in the MPSRCH program (Oxford Molecular), using an affine gap search with parameters gap open penalty=12 and gap extension penalty=1.

Depending on the particular SEQ ID NO, the fragments of (ii) should comprise at least n consecutive amino acids from the sequences and, depending on the particular sequence, n is 7 or more (e.g. 8, 10, 12, 14, 16, 18, 20, 22, 24, 26, 28, 30, 35, 40, 45, 50, 60, 70, 80, 90, 100 or more). The fragment may comprise at least one T-cell or, preferably, a B-cell epitope of the sequence. T- and B-cell epitopes can be identified empirically (e.g. using PEPSCAN [196,197] or similar methods), or they can be predicted (e.g. using the Jameson-Wolf antigenic index [198], matrix-based approaches [199], TEPITOPE [200], neural networks [201], OptiMer & EpiMer [202, 203], ADEPT [204], Tsites [205], hydrophilicity [206], antigenic index [207] or the methods disclosed in reference 208 etc.). Other preferred fragments are SEQ ID NOs 1 to 5 without their N-terminal amino acid residue or without their N-terminal signal peptide. Removal of one or more domains, such as a leader or signal sequence region, a transmembrane region, a cytoplasmic region or a cell wall anchoring motif can be used. Preferred fragments are given below (SEQ ID NOs 6 to 19).

These polypeptide may, compared to SEQ ID NOs 1 to 5, include one or more (e.g. 1, 2, 3, 4, 5, 6, 7, 8, 9, 10, etc.) conservative amino acid replacements i.e. replacements of one amino acid with another which has a related side chain. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cystine, serine, threonine, tyrosine. Phenylalanine, tryptophan, and tyrosine are sometimes classified jointly as aromatic amino acids. In general, substitution of single amino acids within these families does not have a major effect on the biological activity. The polypeptides may also include one or more (e.g. 1, 2, 3, 4, 5, 6, 7, 8, 9, 10, etc.) single amino acid deletions relative to SEQ ID NOs 1 to 5. The polypeptides may also include one or more (e.g. 1, 2, 3, 4, 5, 6, 7, 8, 9, 10, etc.) insertions (e.g. each of 1, 2, 3, 4 or 5 amino acids) relative to the SEQ ID NOs 1 to 5.

Polypeptides of the invention can be prepared in many ways e.g. by chemical synthesis (in whole or in part), by digesting longer polypeptides using proteases, by translation from RNA, by purification from cell culture (e.g. from recombinant expression), from the organism itself (e.g. after bacterial culture, or direct from patients), etc. A preferred method for production of peptides <40 amino acids long involves in vitro chemical synthesis [209,210]. Solid-phase peptide synthesis is particularly preferred, such as methods based on tBoc or Fmoc [211] chemistry. Enzymatic synthesis [212] may also be used in part or in full. As an alternative to chemical synthesis, biological synthesis may be used e.g. the polypeptides may be produced by translation. This may be carried out in vitro or in vivo. Biological methods are in general restricted to the production of polypeptides based on L-amino acids, but manipulation of translation machinery (e.g. of aminoacyl tRNA molecules) can be used to allow the introduction of D-amino acids (or of other non natural amino acids, such as iodotyrosine or methylphenylalanine, azidohomoalanine, etc.) [213]. Where D-amino acids are included, however, it is preferred to use chemical synthesis. Polypeptides of the invention may have covalent modifications at the C-terminus and/or N-terminus.

If these GBS proteins are included in compositions of the invention then they can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.). They are preferably used in purified or substantially purified form i.e. substantially free from other polypeptides (e.g. free from naturally-occurring polypeptides), particularly from other GBS or host cell polypeptides).

GBS67

Nucleotide and amino acid sequence of GBS67 sequenced from serotype V strain 2603 V/R are set forth in ref. 93 as SEQ ID NOs 3745 & 3746. The amino acid sequence is SEQ ID NO:1 herein:

```
MRKYQKFSKILTLSLFCLSQIPLNTNVLGESTVPENGAKGKLVVKKTDDQNKPLSKATFVLKTTAHPESKIEKVTAELT

GEATFDNLIPGDYTLSEETAPEGYKKTNQTWQVKVESNGKTTIQNSGDKNSTIGQNQEELDKQYPPTGIYEDTKESYKL

EHVKGSVPNGKSEAKAVNPYSSEGEHIREIPEGTLSKRISEVGDLAHNKYKIELTVSGKTIVKPVDKQKPLDVVFVLDN

SNSMNNDGPNFQRHNKAKKAAEALGTAVKDILGANSDNRVALVTYGSDIFDGRSVDVVKGFKEDDKYYGLQTKFTIQTE

NYSHKQLTNNAEEIIKRIPTEAPKAKWGSTTNGLTPEQQKEYYLSKVGETFTMKAFMEADDILSQVNRNSQKIIVHVTD

GVPTRSYAINNFKLGASYESQFEQMKKNGYLNKSNFLLTDKPEDIKGNGESYFLFPLDSYQTQIISGNLQKLHYLDLNL

NYPKGTIYRNGPVKEHGTPTKLYINSLKQKNYDIFNFGIDISGFRQVYNEEYKKNQDGTFQKLKEEAFKLSDGEITELM

RSFSSKPEYYTPIVTSADTSNNEILSKIQQQFETILTKENSIVNGTIEDPMGDKINLQLGNGQTLQPSDYTLQGNDGSV

MKDGIATGGPNNDGGILKGVKLEYIGNKLYVRGLNLGEGQKVTLTYDVKLDDSFISNKFYDTNGRTTLNPKSEDPNTLR

DFPIPKIRDVREYPTITIKNEKKLGEIEFIKVDKDNNKLLLKGATFELQEFNEDYKLYLPIKNNNSKVVTGENGKISYK

DLKDGKYQLIEAVSPEDYQKITNKPILTFEVVKGSIKNIIAVNKQISEYHEEGDKHLITNTHIPPKGI*IPMTGGKGILS*

*FILIGGAMMSIAGGIYI*WKRYKKSSDMSIKKD
```

GBS67 contains a C-terminus transmembrane region which is indicated by the underlined region closest to the C-terminus of SEQ ID NO: 1 above. One or more amino acids from the transmembrane region may be removed, or the amino acid may be truncated before the transmembrane region. An example of such a GBS67 fragment is set forth below as SEQ ID NO: 18.

```
MRKYQKFSKILTLSLFCLSQIPLNTNVLGESTVPENGAKGKLVVKKTDDQNKPLSKATFVLKTTAHPESKIEKVTAELT

GEATFDNLIPGDYTLSEETAPEGYKKTNQTWQVKVESNGKTTIQNSGDKNSTIGQNQEELDKQYPPTGIYEDTKESYKL

EHVKGSVPNGKSEAKAVNPYSSEGEHIREIPEGTLSKRISEVGDLAHNKYKIELTVSGKTIVKPVDKQKPLDVVFVLDN

SNSMNNDGPNFQRHNKAKKAAEALGTAVKDILGANSDNRVALVTYGSDIFDGRSVDVVKGFKEDDKYYGLQTKFTIQTE

NYSHKQLTNNAEEIIKRIPTEAPKAKWGSTTNGLTPEQQKEYYLSKVGETFTMKAFMEADDILSQVNRNSQKIIVHVTD

GVPTRSYAINNFKLGASYESQFEQMKKNGYLNKSNFLLTDKPEDIKGNGESYFLFPLDSYQTQIISGNLQKLHYLDLNL

NYPKGTIYRNGPVKEHGTPTKLYINSLKQKNYDIFNFGIDISGFRQVYNEEYKKNQDGTFQKLKEEAFKLSDGEITELM

RSFSSKPEYYTPIVTSADTSNNEILSKIQQQFETILTKENSIVNGTIEDPMGDKINLQLGNGQTLQPSDYTLQGNDGSV
```

-continued

```
MKDGIATGGPNNDGGILKGVKLEYIGNKLYVRGLNLGEGQKVTLTYDVKLDDSFISNKFYDTNGRTTLNPKSEDPNTLR

DFPIPKIRDVREYPTITIKNEKKLGEIEFIKVDKDNNKLLLKGATFELQEFNEDYKLYLPIKNNNSKVVTGENGKISYK

DLKDGKYQLIEAVSPEDYQKITNKPILTFEVVKGSIKNIIAVNKQISEYHEEGDKHLITNTHIPPKGIIPMTGGKGILS
```

GBS67 contains an amino acid motif indicative of a cell wall anchor, shown in italics in SEQ ID NO: 1 above. In some recombinant host cell systems, it may be preferable to remove this motif to facilitate secretion of a recombinant GBS67 protein from the host cell. Accordingly, in one preferred fragment of GBS67 for use in the invention, the transmembrane and the cell wall anchor motif are removed from GBS67. An example of such a GBS67 fragment is set forth below as SEQ ID NO: 19.

```
MRKYQKFSKILTLSLFCLSQIPLNTNVLGESTVPENGAKGKLVVKKTDDQNKPLSKATFVLKTTAHPESKIEKVTAELT

GEATFDNLIPGDYTLSEETAPEGYKKTNQTWQVKVESNGKTTIQNSGDKNSTIGQNQEELDKQYPPTGIYEDTKESYKL

EHVKGSVPNGKSEAKAVNPYSSEGEHIREIPEGTLSKRISEVGDLAHNKYKIELTVSGKTIVKPVDKQKPLDVVFVLDN

SNSMNNDGPNFQRHNKAKKAAEALGTAVKDILGANSDNRVALVTYGSDIFDGRSVDVVKGFKEDDKYYGLQTKFTIQTE

NYSHKQLTNNAEEIIKRIPTEAPKAKWGSTTNGLTPEQQKEYYLSKVGETFTMKAFMEADDILSQVNRNSQKIIVHVTD

GVPTRSYAINNFKLGASYESQFEQMKKNGYLNKSNFLLTDKPEDIKGNGESYFLFPLDSYQTQIISGNLQKLHYLDLNL

NYPKGTIYRNGPVKEHGTPTKLYINSLKQKNYDIFNFGIDISGFRQVYNEEYKKNQDGTFQKLKEEAFKLSDGEITELM

RSFSSKPEYYTPIVTSADTSNNEILSKIQQQFETILTKENSIVNGTIEDPMGDKINLQLGNGQTLQPSDYTLQGNDGSV

MKDGIATGGPNNDGGILKGVKLEYIGNKLYVRGLNLGEGQKVTLTYDVKLDDSFISNKFYDTNGRTTLNPKSEDPNTLR

DFPIPKIRDVREYPTITIKNEKKLGEIEFIKVDKDNNKLLLKGATFELQEFNEDYKLYLPIKNNNSKVVTGENGKISYK

DLKDGKYQLIEAVSFEDYQKITNKPILTFEVVKGSIKNIIAVNKQISEYHEEGDKHLITNTHIPPKGI
```

GBS80

GBS80 refers to a putative cell wall surface anchor family protein. Nucleotide and amino acid sequence of GBS80 sequenced from serotype V isolated strain 2603 V/R are set forth in ref. 93 as SEQ ID NOs 8779 & 8780. The amino acid sequence is set forth below as SEQ ID NO: 2:

```
MKLSKKLLFSAAVLTMVAGSTVEPVAQFATGMSIVRAAEVSQERPAKTTVNIYKLQADSYKSEITSNGGIENKDGEVIS

NYAKLGDNVKGLQGVQFKRYKVKTDISVDELKKLTTVEAADAKVGTILEEGVSLPQKTNAQGLVVDALDSKSNVRYLYV

EDLKNSPSNITKAYAVPFVLELPVANSTGTGFLSEINIYPKNVVTDEPKTDKDVKKLGQDDAGYTIGEEFKWFLKSTIP

ANLGDYEKFEITDKFADGLTYKSVGKIKIGSKTLNRDEHYTIDEPTVDNQNTLKITFKPEKFKEIAELLKGMTLVKNQD

ALDKATANTDDAAFLEIPVASTINEKAVLGKAIENTFELQYDHTPDKADNPKPSNPPRKPEVHTGGKRFVKKDSTETQT

LGGAEFDLLASDGTAVKWTDALIKANTNKNYIAGEAVTGQPIKLKSHTDGTFEIKGLAYAVDANAEGTAVTYKLKETKA

PEGYVIPDKEIEFTVSQTSYNTKPTDITVDSADATPDTIKNNKRPSIPNTGGIGTAIFVAIGAAVMAFAVKGMKRRTKD

N
```

GBS80 contains a N-terminal leader or signal sequence region which is indicated by the underlined sequence above. One or more amino acids from the leader or signal sequence region of GBS80 can be removed. An example of such a GBS80 fragment is set forth below as SEQ ID NO: 6:

```
AEVSQERPAKTTVNIYKLQADSYKSEITSNGGIENKDGEVISNYAKLGDNVKGLQGVQFKRYKVKTDISVDELKKLTTV

EAADAKVGTILEEGVSLPQKTNAQGLVVDALDSKSNVRYLYVEDLKNSPSNITKAYAVPFVLELPVANSTGTGFLSEIN

IYPKNVVTDEPKTDKDVKKLGQDDAGYTIGEEFKWFLKSTIPANLGDYEKFEITDKFADGLTYKSVGKIKIGSKTLNRD

EHYTIDEPTVDNQNTLKITFKPEKFKEIAELLKGMTLVKNQDALDKATANTDDAAFLEIPVASTINEKAVLGKAIENTF

ELQYDHTPDKADNPKPSNPPRKPEVHTGGKRFVKKDSTETQTLGGAEFDLLASDGTAVKWTDALIKANTNKNYIAGEAV
```

-continued

TGQPIKLKSHTDGTFEIKGLAYAVDANAEGTAVTYKLKETKAPEGYVIPDKEIEFTVSQTSYNTKPTDITVDSADATPD

TIKNNKRPSIPNTGGIGTAIFVAIGAAVMAFAVKGMKRRTKDN

GBS80 contains a C-terminal transmembrane region which is indicated by the underlined sequence near the end of SEQ ID NO: 2 above. One or more amino acids from the transmembrane region and/or a cytoplasmic region may be removed. An example of such a fragment is set forth below as SEQ ID NO:7:

MKLSKKLLFSAAVLTMVAGSTVEPVAQFATGMSIVRAAEVSQERPAKTTVNIYKLQADSYKSEITSNGGIENKDGEVIS

NYAKLGDNVKGLQGVQFKRYKVKTDISVDELKKLTTVEAADAKVGTILEEGVSLPQKTNAQGLVVDALDSKSNVRYLYV

EDLKNSPSNITKAYAVPFVLELPVANSTGTGFLSEINIYPKNVVTDEPKTDKDVKKLGQDDAGYTIGEEFKWFLKSTIP

ANLGDYEKFEITDKFADGLTYKSVGKIKIGSKTLNRDEHYTIDEPTVDNQNTLKITFKPEKFKEIAELLKGMTLVKNQD

ALDKATANTDDAAFLEIPVASTINEKAVLGKAIENTFELQYDHTPDKADNPKPSNPPRKPEVHTGGKRFVKKDSTETQT

LGGAEFDLLASDGTAVKWTDALIKANTNKNYIAGEAVTGQPIKLKSHTDGTFEIKGLAYAVDANAEGTAVTYKLKETKA

PEGYVIPDKEIEFTVSQTSYNTKPTDITVDSADATPDTIKNNKRPS*IPNTG*

GBS80 contains an amino acid motif indicative of a cell wall anchor, shown in italics in SEQ ID NO: 2 above. In some recombinant host cell systems, it may be preferable to remove this motif to facilitate secretion of a recombinant GBS80 protein from the host cell. Thus the transmembrane and/or cytoplasmic regions and the cell wall anchor motif may be removed from GBS80. An example of such a fragment is set forth below as SEQ ID NO: 8.

MKLSKKLLFSAAVLTMVAGSTVEPVAQFATGMSIVRAAEVSQERPAKTTVNIYKLQADSYKSEITSNGGIENKDGEVIS

NYAKLGDNVKGLQGVQFKRYKVKTDISVDELKKLTTVEAADAKVGTILEEGVSLPQKTNAQGLVVDALDSKSNVRYLYV

EDLKNSPSNITKAYAVPFVLELPVANSTGTGFLSEINIYPKNVVTDEPKTDKDVKKLGQDDAGYTIGEEFKWFLKSTIP

ANLGDYEKFEITDKFADGLTYKSVGKIKIGSKTLNRDEHYTIDEPTVDNQNTLKITFKPEKFKEIAELLKGMTLVKNQD

ALDKATANTDDAAFLEIPVASTINEKAVLGKAIENTFELQYDHTPDKADNPKPSNPPRKPEVHTGGKRFVKKDSTETQT

LGGAEFDLLASDGTAVKWTDALIKANTNKNYIAGEAVTGQPIKLKSHTDGTFEIKGLAYAVDANAEGTAVTYKLKETKA

PEGYVIPDKEIEFTVSQTSYNTKPTDITVDSADATPDTIKNNKRPS

Alternatively, in some recombinant host cell systems, it may be preferable to use the cell wall anchor motif to anchor the recombinantly expressed protein to the cell wall. The extracellular domain of the expressed protein may be cleaved during purification or the recombinant protein may be left attached to either inactivated host cells or cell membranes in the final composition.

In one embodiment, the leader or signal sequence region, the transmembrane and cytoplasmic regions and the cell wall anchor motif are removed from the GBS80 sequence. An example of such a GBS80 fragment is set forth below as SEQ ID NO: 9:

AEVSQERPAKTTVNIYKLQADSYKSEITSNGGIENKDGEVISNYAKLGDNVKGLQGVQFKRYKVKTDISVDELKKLTTV

EAADAKVGTILEEGVSLPQKTNAQGLVVDALDSKSNVRYLYVEDLKNSPSNITKAYAVPFVLELPVANSTGTGFLSEIN

IYPKNVVTDEPKTDKDVKKLGQDDAGYTIGEEFKWFLKSTIPANLGDYEKFEITDKFADGLTYKSVGKIKIGSKTLNRD

EHYTIDEPTVDNQNTLKITFKPEKFKEIAELLKGMTLVKNQDALDKATANTDDAAFLEIPVASTINEKAVLGKAIENTF

ELQYDHTPDKADNPKPSNPPRKPEVHTGGKRFVKKDSTETQTLGGAEFDLLASDGTAVKWTDALIKANTNKNYIAGEAV

TGQPIKLKSHTDGTFEIKGLAYAVDANAEGTAVTYKLKETKAPEGYVIPDKEIEFTVSQTSYNTKPTDITVDSADATPD

TIKNNKRPS

A particularly immunogenic fragment of GBS80 is located towards the N-terminus of the protein, and is given herein as SEQ ID NO: 10:

```
AEVSQERPAKTTVNIYKLQADSYKSEITSNGGIENKDGEVISNYAKLGDNVKGLQGVQFKRYKVKTDISVDELKKLTTV

EAADAKVGTILEEGVSLPQKTNAQGLVVDALDSKSNVRYLYVEDLKNSPSNITKAYAVPFVLELPVANSTGTGFLSEIN

IYPKNVVTDEPKTDKDVKKLGQDDAGYTIGEEFKWFLKSTIPANLGDYEKFEITDKFADGLTYKSVGKIKIGSKTLNRD

EHYTIDEPTVDNQNTLKITFKPEKFKEIAELLKG
```

GBS104

GBS104 refers to a putative cell wall surface anchor family protein. It has been referred to as emaA. Nucleotide and amino acid sequences of GBS104 sequenced from serotype V isolated strain 2603 V/R are set forth in Ref. 93 as SEQ ID 8777 and SEQ ID 8778. The amino acid sequence is SEQ ID NO: 3 herein:

```
MKKRQKIWRGLSVTLLILSQIPFGILVQGETQDTNQALGKVIVKKTGDNATPLGKATFVLKNDNDKSETSHETVEGSGE

ATFENIKPGDYTLREETAPIGYKKTDKTWKVKVADNGATIIEGMDADKAEKRKEVLNAQYPKSAIYEDTKENYPLVNVE

GSKVGEQYKALNPINGKDGRREIAEGWLSKKITGVNDLDKNKYKIELTVEGKTTVETKELNQPLDVVVLLDNSNSMNNE

RANNSQRALKAGEAVEKLIDKITSNKDNRVALVTYASTIFDGTEATVSKGVADQNGKALNDSVSWDYHKTTFTATTHNY

SYLNLTNDANEVNILKSRIPKEAEHINGDRTLYQFGATFTQKALMKANEILETQSSNARKKLIFHVTDGVPTMSYAINF

NPYISTSYQNQFNSFLNKIPDRSGILQEDFIINGDDYQIVKGDGESFKLFSDRKVPVTGGTTQAAYRVPQNQLSVMSNE

GYAINSGYIYLYWRDYNWVYPFDPKTKKVSATKQIKTHGEPTTLYFNGNIRPKGYDIFTVGIGVNGDPGATPLEAEKFM

QSISSKTENYTNVDDTNKIYDELNKYFKTIVEEKHSIVDGNVTDPMGEMIEFQLKNGQSFTHDDYVLVGNDGSQLKNGV

ALGGPNSDGGILKDVTVTYDKTSQTIKINHLNLGSGQKVVLTYDVRLKDNYISNKFYNTNNRTTLSPKSEKEPNTIRDF

PIPKIRDVREFPVLTISNQKKMGEVEFIKVNKDKHSESLLGAKFQLQIEKDFSGYKQFVPEGSDVTTKNDGKIYFKALQ

DGNYKLYEISSPDGYIEVKTKPVVTFTIQNGEVTNLKADPNANKNQIGYLEGNGKHLITNTPKRPPGVFPKTGGIGTIV

YILVGSTFMILTICSFRRKQL
```

GBS104 contains an N-terminal leader or signal sequence region which is indicated by the underlined sequence at the beginning of SEQ ID NO: 3 above. One or more amino acids from the leader or signal sequence region of GBS104 may be removed. An example of such a GBS104 fragment is set forth below as SEQ ID NO 11.

```
GETQDTNQALGKVIVKKTGDNATPLGKATFVLKNDNDKSETSHETVEGSGEATFENIKPGDYTLREETAPIGYKKTDKT

WKVKVADNGATIIEGMDADKAEKRKEVLNAQYPKSAIYEDTKENYPLVNVEGSKVGEQYKALNPINGKDGRREIAEGWL

SKKITGVNDLDKNKYKIELTVEGKTTVETKELNQPLDVVVLLDNSNSMNNERANNSQRALKAGEAVEKLIDKITSNKDN

RVALVTYASTIFDGTEATVSKGVADQNGKALNDSVSWDYHKTTFTATTHNYSYLNLTNDANEVNILKSRIPKEAEHING

DRTLYQFGATFTQKALMKANEILETQSSNARKKLIFHVTDGVPTMSYAINFNPYISTSYQNQFNSFLNKIPDRSGILQE

DFIINGDDYQIVKGDGESFKLFSDRKVPVTGGTTQAAYRVPQNQLSVMSNEGYAINSGYIYLYWRDYNWVYPFDPKTKK

VSATKQIKTHGEPTTLYFNGNIRPKGYDIFTVGIGVNGDPGATPLEAEKFMQSISSKTENYTNVDDTNKIYDELNKYFK

TIVEEKHSIVDGNVTDPMGEMIEFQLKNGQSFTHDDYVLVGNDGSQLKNGVALGGPNSDGGILKDVTVTYDKTSQTIKI

NHLNLGSGQKVVLTYDVRLKDNYISNKFYNTNNRTTLSPKSEKEPNTIRDFPIPKIRDVREFPVLTISNQKKMGEVEFI

KVNKDKHSESLLGAKFQLQIEKDFSGYKQFVPEGSDVTTKNDGKIYFKALQDGNYKLYEISSPDGYIEVKTKPVVTFTI

QNGEVTNLKADPNANKNQIGYLEGNGKHLITNTPKRPPGVFPKTGGIGTIVYILVGSTFMILTICSFRRKQL
```

GBS104 contains a C-terminal transmembrane and/or cytoplasmic region which is indicated by the underlined region near the end of SEQ ID NO:3 above. One or more amino acids from the transmembrane or cytoplasmic regions may be removed. An example of such a GBS104 fragment is set forth below as SEQ ID NO 12:

MKKRQKIWRGLSVTLLILSQIPFGILVQGETQDTNQALGKVIVKKTGDNATPLGKATFVLKNDNDKSETSHETVEGSGE

ATFENIKPGDYTLREETAPIGYKKTDKTWKVKVADNGATIIEGMDADKAEKRKEVLNAQYPKSAIYEDTKENYPLVNVE

GSKVGEQYKALNPINGKDGRREIAEGWLSKKITGVNDLDKNKYKIELTVEGKTTVETKELNQPLDVVVLLDNSNSMNNE

RANNSQRALKAGEAVEKLIDKITSNKDNRVALVTYASTIFDGTEATVSKGVADQNGKALNDSVSWDYHKTTFTATTHNY

SYLNLTNDANEVNILKSRIPKEAEHINGDRTLYQFGATFTQKALMKANEILETQSSNARKKLIFHVTDGVPTMSYAINF

NPYISTSYQNQFNSFLNKIPDRSGILQEDFIINGDDYQIVKGDGESFKLFSDRKVPVTGGTTQAAYRVPQNQLSVMSNE

GYAINSGYIYLYWRDYNWVYPFDPKTKKVSATKQIKTHGEPTTLYFNGNIRPKGYDIFTVGIGVNGDPGATPLEAEKFM

QSISSKTENYTNVDDTNKIYDELNKYFKTIVEEKHSIVDGNVTDPMGEMIEFQLKNGQSFTHDDYVLVGNDGSQLKNGV

ALGGPNSDGGILKDVTVTYDKTSQTIKINHLNLGSGQKVVLTYDVRLKDNYISNKFYNTNNRTTLSPKSEKEPNTIRDF

PIPKIRDVREFPVLTISNQKKMGEVEFIKVNKDKHSESLLGAKFQLQIEKDFSGYKQFVPEGSDVTTKNDGKIYFKALQ

DGNYKLYEISSPDGYIEVKTKPVVTFTIQNGEVTNLKADPNANKNQIGYLEGNGKHLITNT

One or more amino acids from the leader or signal sequence region and one or more amino acids from the transmembrane or cytoplasmic regions may be removed. An example of such a GBS104 fragment is set forth below as SEQ ID NO 13:

GETQDTNQALGKVIVKKTGDNATPLGKATFVLKNDNDKSETSHETVEGSGEATFENIKPGDYTLREETAPIGYKKTDKT

WKVKVADNGATIIEGMDADKAEKRKEVLNAQYPKSAIYEDTKENYPLVNVEGSKVGEQYKALNPINGKDGRREIAEGWL

SKKITGVNDLDKNKYKIELTVEGKTTVETKELNQPLDVVVLLDNSNSMNNERANNSQRALKAGEAVEKLIDKITSNKDN

RVALVTYASTIFDGTEATVSKGVADQNGKALNDSVSWDYHKTTFTATTHNYSYLNLTNDANEVNILKSRIPKEAEHING

DRTLYQFGATFTQKALMKANEILETQSSNARKKLIFHVTDGVPTMSYAINFNPYISTSYQNQFNSFLNKIPDRSGILQE

DFIINGDDYQIVKGDGESFKLFSDRKVPVTGGTTQAAYRVPQNQLSVMSNEGYAINSGYIYLYWRDYNWVYPFDPKTKK

VSATKQIKTHGEPTTLYFNGNIRPKGYDIFTVGIGVNGDPGATPLEAEKFMQSISSKTENYTNVDDTNKIYDELNKYFK

TIVEEKHSIVDGNVTDPMGEMIEFQLKNGQSFTHDDYVLVGNDGSQLKNGVALGGPNSDGGILKDVTVTYDKTSQTIKI

NHLNLGSGQKVVLTYDVRLKDNYISNKFYNTNNRTTLSPKSEKEPNTIRDFPIPKIRDVREFPVLTISNQKKMGEVEFI

KVNKDKHSESLLGAKFQLQIEKDFSGYKQFVPEGSDVTTKNDGKIYFKALQDGNYKLYEISSPDGYIEVKTKPVVTFTI

QNGEVTNLKADPNANKNQIGYLEGNGKHLITNT

Further fragments of GBS104 include an 830 amino acid fragment of GBS104 of amino acids 28-858 (numbered by SEQ ID NO: 3), a 359 amino acid fragment of GBS104 of amino acids 28-387, a 581 amino acid fragment of GBS104 of amino acids 28-609, or a 740 amino acid fragment of GBS104 of amino acids 28-768.

GBS276

GBS276 refers to a C5a peptidase. Further description of GBS276 can be found in references 214-217. Nucleotide and amino acid sequences of GBS276 sequenced from serotype V isolated strain 2603 V/R are set forth in Ref. 93 as SEQ ID NOs 8941 & 8942. The amino acid sequence is SEQ ID NO: 4 herein:

MRKKQKLPFDKLAIALISTSILLNAQSDIKANTVTEDTPATEQAVEPPQPIAVSEESRSSKETKTSQTPSDVGETVADD

ANDLAPQAPAKTADTPATSKATIRDLNDPSHVKTLQEKAGKGAGTVVAVIDAGFDKNHEAWRLTDKTKARYQSKENLEK

AKKEHGITYGEWVNDKVAYYHDYSKDGKNAVDQEHGTHVSGILSGNAPSEMKEPYRLSGAMPEAQLLLMRVEIVNGLAD

YARNYAQAIRDAVNLGAKVINMSFGNAALAYANLPDETKKAFDYAKSKGVSIVTSAGNDSSFGGKPRLPLADHPDYGVV

GTPAAADSTLTVASYSPDKQLTETATVKTDDHQDKEMPVISTNRFEPNKAYDYAYANRGTKEDDFKDVSGKIALIERGD

-continued

```
IDFKDKIANAKKAGAVGVLIYDNQDKGFPIELPNVDQMPAAFISRRDGLLLKDNPPKTITFNATPKVLPTASGTKLSRF

SSWGLTADGNIKPDIAAPGQDILSSVANNKYAKLSGTSMSAPLVAGIMGLLQKQYETQYPDMTPSERLDLAKKVLMSSA

TALYDEDEKAYFSPRQQGAGAVDAKKASAATMYVTDKDNTSSKVHLNNVSDKFEVTVTVHNKSDKPQELYYQVTVQTDK

VDGKHFALAPKALYETSWQKITIPANSSKQVTVPIDASRFSKDLLAQMKNGYFLEGFVRFKQDPTKEELMSIPYIGFRG

DFGNLSALEKPIYDSKDGSSYYHEANSDAKDQLDGDGLQFYALKNNFTALTTESNPWTIIKAVKEGVENIEDIESSEIT

ETIFAGTFAKQDDDSHYYIHRHANGKPYAAISPNGDGNRDYVQFQGTFLRNAKNLVAEVLDKEGNVVWTSEVTEQVVKN

YNNDLASTLGSTRFEKTRWDGKDKDGKVVANGTYTYRVRYTPISSGAKEQHTDFDVIVDNTTPEVATSATFSTEDSRLT

LASKPKTSQPVYRERIAYTYMDEDLPTTEYISPNEDGTFTLPEEAETMEGATVPLKMSDFTYVVEDMAGNITYTPVTKL

LEGHSNKPEQDGSDQAPDKKPEAKPEQDGSGQTPDKKKETKPEKDSSGQTPGKTPQKGQSSRTLEKRSSKRALATKAST

RDQLPTTNDKDTNRLHLLKLVMTTFFLG
```

GBS276 contains an N-terminal leader or signal sequence region which is indicated by the underlined sequence at the beginning of SEQ ID NO: 4 above. One or more amino acids from the leader or signal sequence region of GBS276 may be removed. An example of such a GBS276 fragment is set forth below as SEQ ID NO: 14:

```
QSDIKANTVTEDTPATEQAVEPPQPIAVSEESRSSKETKTSQTPSDVGETVADDANDLAPQAPAKTADTPATSKATIRD

LNDPSHVKTLQEKAGKGAGTVVAVIDAGFDKNHEAWRLTDKTKARYQSKENLEKAKKEHGITYGEWVNDKVAYYHDYSK

DGKNAVDQEHGTHVSGILSGNAPSEMKEPYRLEGAMPEAQLLLMRVEIVNGLADYARNYAQAIRDAVNLGAKVINMSFG

NAALAYANLPDETKKAFDYAKSKGVSIVTSAGNDSSFGGKPRLPLADHPDYGVVGTPAAADSTLTVASYSPDKQLTETA

TVKTDDHQDKEMPVISTNRFEPNKAYDYAYANRGTKEDDFKDVEGKIALIERGDIDFKDKIANAKKAGAVGVLIYDNQD

KGFPIELPNVDQMPAAFISRRDGLLLKDNPPKTITFNATPKVLPTASGTKLSRFSSWGLTADGNIKPDIAAPGQDILSS

VANNKYAKLSGTSMSAPLVAGIMGLLQKQYETQYPDMTPSERLDLAKKVLMSSATALYDEDEKAYFSPRQQGAGAVDAK

KASAATMYVTDKDNTSSKVHLNNVSDKFEVTVTVHNKSDKPQELYYQVTVQTDKVDGKHFALAPKALYETSWQKITIPA

NSSKQVTVPIDASRFSKDLLAQMKNGYFLEGFVRFKQDPTKEELMSIPYIGFRGDFGNLSALEKPIYDSKDGSSYYHEA

NSDAKDQLDGDGLQFYALKNNFTALTTESNPWTIIKAVKEGVENIEDIESSEITETIFAGTFAKQDDDSHYYIHRHANG

KPYAAISPNGDGNRDYVQFQGTFLRNAKNLVAEVLDKEGNVVWTSEVTEQVVKNYNNDLASTLGSTRFEKTRWDGKDKD

GKVVANGTYTYRVRYTPISSGAKEQHTDFDVIVDNTTPEVATSATFSTEDSRLTLASKPKTSQPVYRERIAYTYMDEDL

PTTEYISPNEDGTFTLPEEAETMEGATVPLKMSDFTYVVEDMAGNITYTPVTKLLEGHSNKPEQDGSDQAPDKKPEAKP

EQDGSGQTPDKKKETKPEKDSSGQTPGKTPQKGQSSRTLEKRSSKRALATKASTRDQLPTTNDKDTNRLHLLKLVMTTF

FLG
```

GBS276 contains a C-terminal transmembrane and/or cytoplasmic region which is indicated by the underlined sequence near the end of SEQ ID NO: 4 above. One or more amino acids from the transmembrane or cytoplasmic regions of GBS276 may be removed. An example of such a GBS276 fragment is set forth below as SEQ ID NO: 15:

```
MRKKQKLPFDKLAIALISTSILLNAQSDIKANTVTEDTPATEQAVEPPQPIAVSEESRSSKETKTSQTPSDVGETVADD

ANDLAPQAPAKTADTPATSKATIRDLNDPSHVKTLQEKAGKGAGTVVAVIDAGFDKNHEAWRLTDKTKARYQSKENLEK

AKKEHGITYGEWVNDKVAYYHDYSKDGKNAVDQEHGTHVSGILSGNAPSEMKEPYRLEGAMPEAQLLLMRVEIVNGLAD

YARNYAQAIRDAVNLGAKVINMSFGNAALAYANLPDETKKAFDYAKSKGVSIVTSAGNDSSFGGKPRLPLADHPDYGVV

GTPAAADSTLTVASYSPDKQLTETATVKTDDHQDKEMPVISTNRFEPNKAYDYAYANRGTKEDDFKDVEGKIALIERGD

IDFKDKIANAKKAGAVGVLIYDNQDKGFPIELPNVDQMPAAFISRRDGLLLKDNPPKTITFNATPKVLPTASGTKLSRF

SSWGLTADGNIKPDIAAPGQDILSSVANNKYAKLSGTSMSAPLVAGIMGLLQKQYETQYPDMTPSERLDLAKKVLMSSA
```

-continued

```
TALYDEDEKAYFSPRQQGAGAVDAKKASAATMYVTDKDNTSSKVHLNNVSDKFEVTVTVHNKSDKPQELYYQVTVQTDK

VDGKHFALAPKALYETSWQKITIPANSSKQVTVPIDASRFSKDLLAQMKNGYFLEGFVRFKQDPTKEELMSIPYIGFRG

DFGNLSALEKPIYDSKDGSSYYHEANSDAKDQLDGDGLQFYALKNNFTALTTESNPWTIIKAVKEGVENIEDIESSEIT

ETIFAGTFAKQDDDSHYYIHRHANGKPYAAISPNGDGNRDYVQFQGTFLRNAKNLVAEVLDKEGNVVWTSEVTEQVVKN

YNNDLASTLGSTRFEKTRWDGKDKDGKVVANGTYTYRVRYTPISSGAKEQHTDFDVIVDNTTPEVATSATFSTEDSRLT

LASKPKTSQPVYRERIAYTYMDEDLPTTEYISPNEDGTFTLPEEAETMEGATVPLKMSDFTYVVEDNAGNITYTPVTKL

LEGHSNKPEQDGSDQAPDKKPEAKPEQDGSGQTPDKKKETKPEKDSSGQTPGKTPQKGQSSRTLEKRSSKRALATK
```

One or more amino acids from the leader or signal sequence region and one or more amino acids from the transmembrane or cytoplasmic regions of GBS276 may be removed. An example of such a GBS276 fragment is set forth below as SEQ ID NO: 16:

```
QSDIKANTVTEDTPATEQAVEPPQPIAVSEESRSSKETKTSQTPSDVGETVADDANDLAPQAPAKTADTPATSKATIRD

LNDPSHVKTLQEKAGKGAGTVVAVIDAGFDKNHEAWRLTDKTKARYQSKENLEKAKKEHGITYGEWVNDKVAYYHDYSK

DGKNAVDQEHGTHVSGILSGNAPSEMKEPYRLEGAMPEAQLLLMRVEIVNGLADYARNYAQAIRDAVNLGAKVINMSFG

NAALAYANLPDETKKAFDYAKSKGVSIVTSAGNDSSFGGKPRLPLADHPDYGVVGTPAAADSTLTVASYSPDKQLTETA

TVKTDDHQDKEMPVISTNRFEPNKAYDYAYANRGTKEDDFKDVEGKIALIERGDIDFKDKIANAKKAGAVGVLIYDNQD

KGFPIELPNVDQMPAAFISRRDGLLLKDNPPKTITFNATPKVLPTASGTKLSRFSSWGLTADGNIKPDIAAPGQDILSS

VANNKYAKLSGTSMSAPLVAGIMGLLQKQYETQYPDMTPSERLDLAKKVLMSSATALYDEDEKAYFSPRQQGAGAVDAK

KASAATMYVTDKDNTSSKVHLNNVSDKFEVTVTVHNKSDKPQELYYQVTVQTDKVDGKHFALAPKALYETSWQKITIPA

NSSKQVTVPIDASRFSKDLLAQMKNGYFLEGFVRFKQDPTKEELMSIPYIGFRGDFGNLSALEKPIYDSKDGSSYYHEA

NSDAKDQLDGDGLQFYALKNNFTALTTESNPWTIIKAVKEGVENIEDIESSEITETIFAGTFAKQDDDSHYYIHRHANG

KPYAAISPNGDGNRDYVQFQGTFLRNAKNLVAEVLDKEGNVVWTSEVTEQVVKNYNNDLASTLGSTRFEKTRWDGKDKD

GKVVANGTYTYRVRYTPISSGAKEQHTDFDVIVDNTTPEVATSATFSTEDSRLTLASKPKTSQPVYRERIAYTYMDEDL

PTTEYISPNEDGTFTLPEEAETMEGATVPLKMSDFTYVVEDMAGNITYTPVTKLLEGHSNKPEQDGSDQAPDKKPEAKP

EQDGSGQTPDKKKETKPEKDSSGQTPGKTPQKGQSSRTLEKRSSKRALATK
```

GBS322.

GBS322 refers to a surface immunogenic protein, also referred to as 'sip'. Nucleotide and amino acid sequences of GBS322 sequenced from serotype V isolated strain 2603 V/R are set forth in Ref. 93 as SEQ ID NOs 8539 & 8540. The amino acid sequence is SEQ ID NO: 5 herein:

```
MNKKVLLTSTMAASLLSVASVQAQETDTTWTARTVSEVKADLVKQDNKSSYTVKYGDTLSVISEAMSIDMNVLAKINNI

ADINLIYPETTLTVTYDQKSHTATSMKIETPATNAAGQTTATVDLKTNQVSVADQKVSLNTISEGMTPEAATTIVSPMK

TYSSAPALKSKBWLAQEQAVSQAAANEQVSPAPVKSITSEVPAAKEEVKPTQTSVSQSTTVSPASVAAETPAPVAKVAP

VRTVAAPRVASVKVVTPKVETGASPEHVSAPAVPVTTTSPATDSKLQATEVKSVPVAQKAPTATPVAQPASTTNAVAAH

PENAGLQPHVAAYKEKVASTYGVNEFSTYRAGDPGDHGKGLAVDFIVGTNQALGNKVAQYSTQNMAANNISYVIWQQKF

YSNTNSIYGPANTWNAMPDRGGVTANHYDHVHVSFNK
```

GBS322 contains a N-terminal leader or signal sequence region which is indicated by the underlined sequence near the beginning of SEQ ID NO: 5. One or more amino acids from the leader or signal sequence region of GBS322 may be removed. An example of such a GBS322 fragment is set forth below as SEQ ID NO: 17:

```
DLVKQDNKSSYTVKYGDTLSVISEAMSIDMNVLAKINNIADINLIYPETTLTVTYDQKSHTATSMKIETPATNAAGQTT

ATVDLKTNQVSVADQKVSLNTISEGMTPEAATTIVSPMKTYSSAPALKSKEVLAQEQAVSQAAANEQVSPAPVKSITSE

VPAAKEEVKPTQTSVSQSTTVSPASVAAETPAPVAKVAPVRTVAAPRVASVKVVTPKVETGASPEHVSAPAVPVTTTSP

ATDSKLQATEVKSVPVAQKAPTATPVAQPASTTNAVAAHPENAGLQPHVAAYKEKVASTYGVNEFSTYRAGDPGDHGKG

LAVDFIVGTNQALGNKVAQYSTQNMAANNISYVIWQQKFYSNTNSIYGPANTWNAMPDRGGVTANHYDHVHVSFNK
```

General

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

Where the invention provides a process involving multiple sequential steps, the invention can also provide a process involving less than the total number of steps. In the first aspect of the invention, for instance, the invention provides a process comprising the steps of: (a) oxidising a GBS capsular saccharide in order to introduce an aldehyde group into a terminal sialic acid residue; and (b) subjecting the aldehyde group to reductive amination. The further steps (c) and (d) need not be performed in order to fall within the scope of the invention, as the product of steps (a) and (b) has utility as an intermediate in conjugate preparation, and may be used, stored, exported, etc. for separate and later use e.g. in steps (c) and (d).

Similarly, where a starting saccharide material is already partially processed then the invention encompasses processes involving only the later steps of a method. In the third aspect of the invention, for instance, the invention encompasses a process comprising a step of coupling a modified galactose residue to a carrier molecule, in which the starting material for the process is a saccharide that was previously oxidised to introduce an aldehyde group into a galactose residue.

These different steps can be performed at very different times by different people in different places (e.g. in different countries).

It will be appreciated that sugar rings can exist in open and closed form and that, whilst closed forms are shown in structural formulae herein, open forms are also encompassed by the invention. Similarly, it will be appreciated that sugars can exist in pyranose and furanose forms and that, whilst pyranose forms are shown in structural formulae herein, furanose forms are also encompassed. Different anomeric forms of sugars are also encompassed.

A primary amine can be represented by formula $NH_2R$. The R group will preferably be electron donating, and includes $C_{1-8}$hydrocarbyl, more preferably $C_{1-8}$alkyl, especially methyl. R is preferably —$CH_3$, —$C_2H_5$ or —$C_3H_7$. The hydrocarbyl may be substituted with one or more groups, such as: halogen (e.g. Cl, Br, F, I), trihalomethyl, —$NO_2$, —CN, —$N^+(C_{1-6}alkyl)_2O^-$, —$SO_3H$, —$SOC_{1-6}alkyl$, —$SO_2C_{1-6}alkyl$, —$SO_3C_{1-6}alkyl$, —OC(=O)O$C_{1-6}alkyl$, —C(=O)H, —C(=O)$C_{1-6}alkyl$, —OC(=O)$C_{1-6}alkyl$, —N($C_{1-6}alkyl)_2$, $C_{1-6}alkyl$, —N($C_{1-6}alkyl)_2$, —C(=O)N($C_{1-6}alkyl)_2$, —N($C_{1-6}alkyl$)C(=O)O($C_{1-6}alkyl$), —N($C_{1-6}alkyl$)C(=O)N($C_{1-6}alkyl)_2$, —$CO_2H$, —OC(=O)N($C_{1-6}alkyl)_2$, —N($C_{1-6}alkyl$)C(=O)$C_{1-6}alkyl$, —N($C_{1-6}alkyl$)C(=S)$C_{1-6}alkyl$, —N($C_{1-6}alkyl$)$SO_2N$($C_{1-6}alkyl)_2$, —$CO_2C_{1-6}alkyl$, —$SO_2N(C_{1-6}alkyl)_2$, —C(=O)$NH_2$, —C(=S)N($C_{1-6}alkyl)_2$, —N($C_{1-6}alkyl$)$SO_2C_{1-6}alkyl$, —N($C_{1-6}alkyl$)C(=S)N($C_{1-6}alkyl)_2$, —NH—$C_{1-6}alkyl$, —S—$C_{1-6}alkyl$ or —O—$C_{1-6}alkyl$. The term 'hydrocarbyl' includes linear, branched or cyclic monovalent groups consisting of carbon and hydrogen. Hydrocarbyl groups thus include alkyl, alkenyl and alkynyl groups, cycloalkyl (including polycycloalkyl), cycloalkenyl and aryl groups and combinations thereof, e.g. alkylcycloalkyl, alkylpolycycloalkyl, alkylaryl, alkenylaryl, cycloalkylaryl, cycloalkenylaryl, cycloalkylalkyl, polycycloalkylalkyl, arylalkyl, arylalkenyl, arylcycloalkyl and arylcycloalkenyl groups. Preferred hydrocarbyl are $C_{1-14}$ hydrocarbyl, more preferably $C_{1-8}$ hydrocarbyl.

BRIEF DESCRIPTION OF DRAWINGS

FIG. 3 shows the repeating structures of capsular saccharides in GBS serotypes Ia, Ib, II, III & V.

FIG. 5A, example of a conjugate in which an individual saccharide is attached to a single carrier. FIG. 5B, example of a conjugate in which an individual saccharide is attached to multiple carriers.

MODES FOR CARRYING OUT THE INVENTION

Conjugate Production and Characterisation

Figure 1:
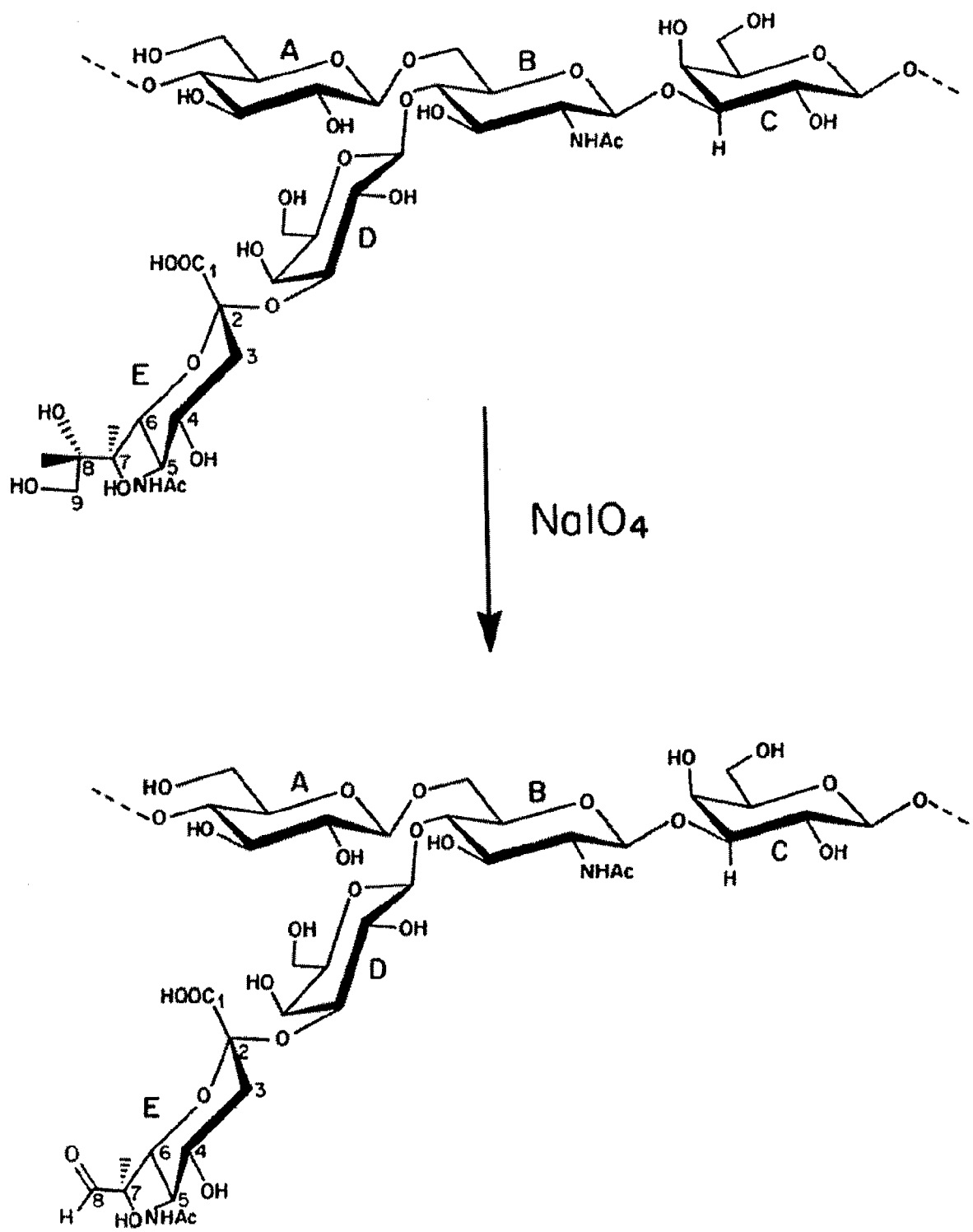
FIG. 1 shows periodate oxidation of a terminal sialic acid residue.
Figure 2:
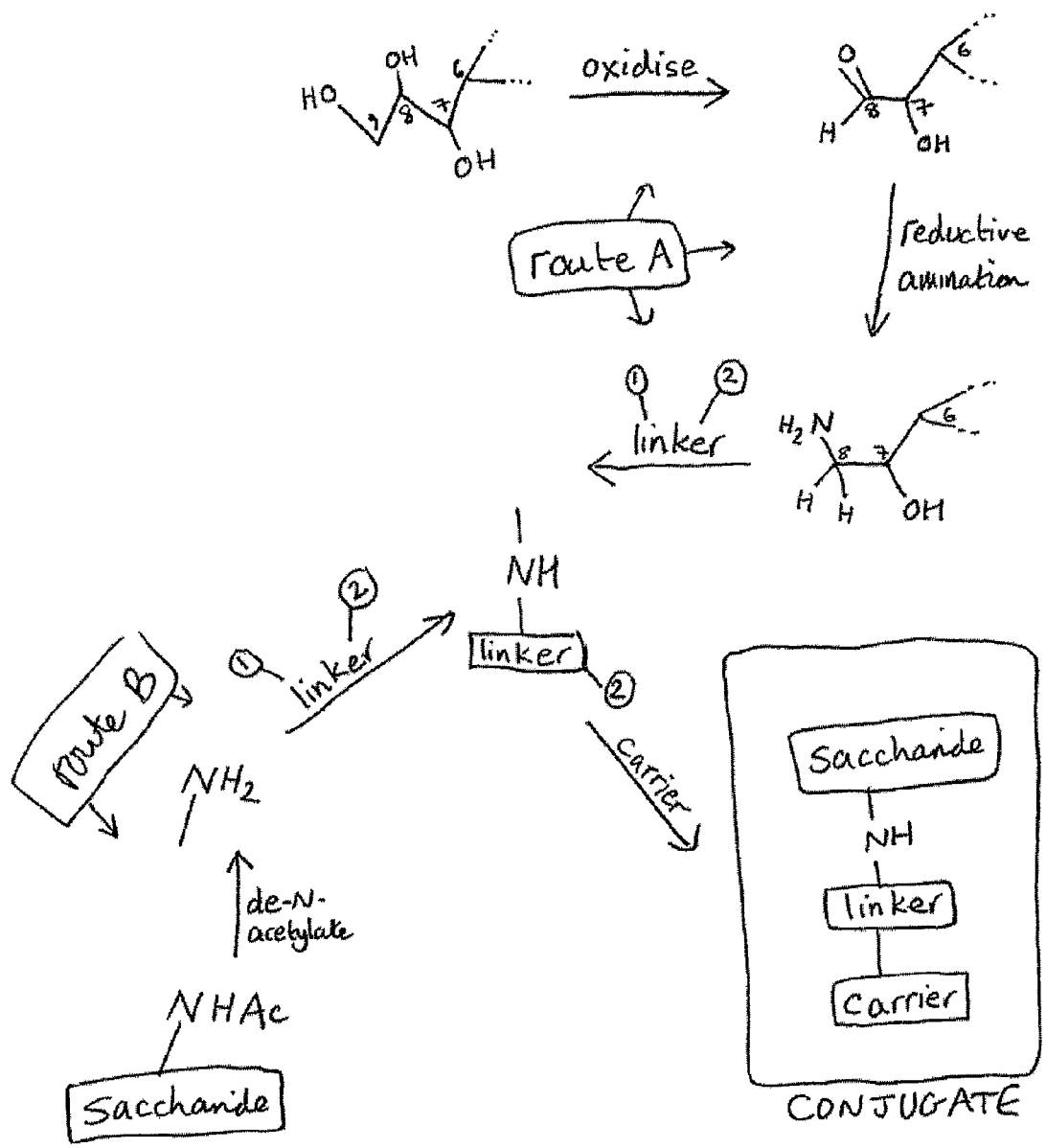
FIG. 2 illustrates the first (route A) and second (route B) aspects of the invention. The numbers at either end of the linkers designate a first group ("1") for coupling to an amine group in the modified capsular saccharide and a second group ("2") for coupling to the carrier. Numbering in the chemical structures refers to the identifying numbers of the depicted carbon atoms.
Figure 4:
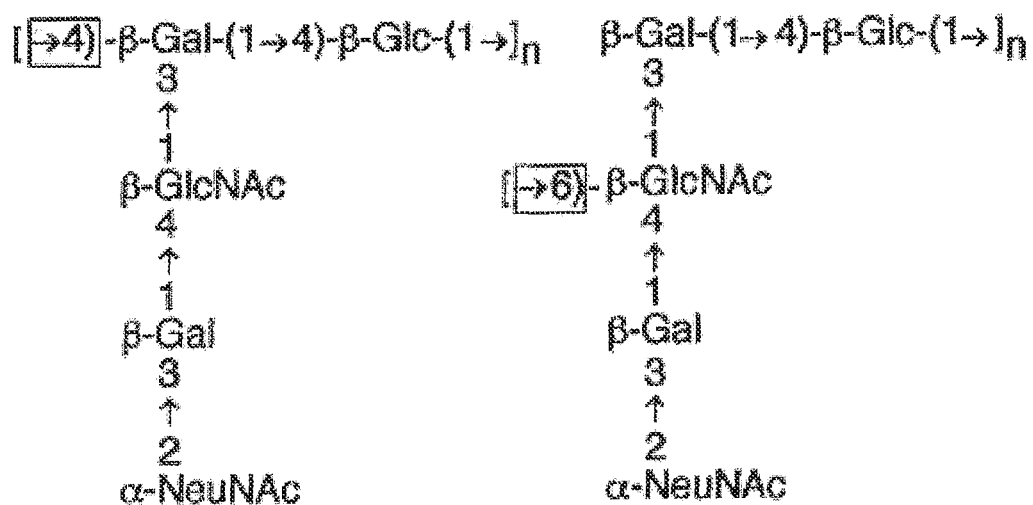
FIG. 4 shows the difference between the repeating structures in GBS serotypes Ia and III.
Figure 5:
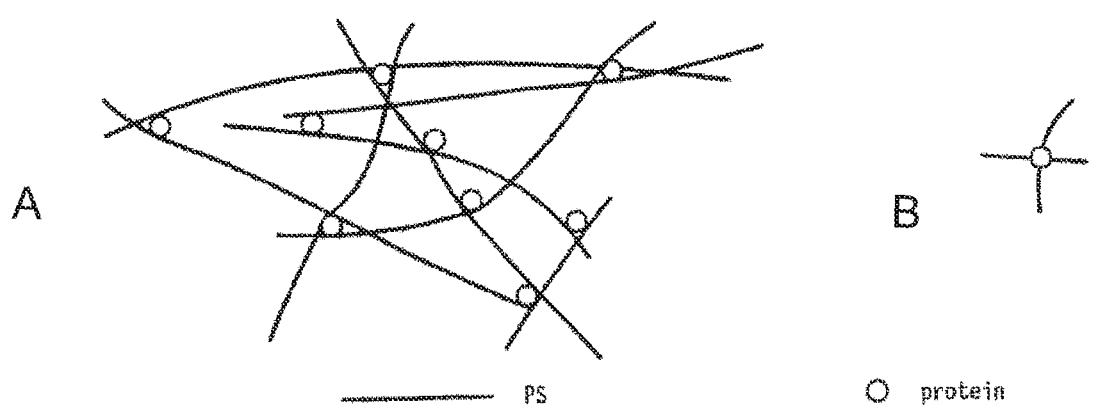
FIGS. 5A-B show two types of conjugate that can be prepared.
Figure 6:
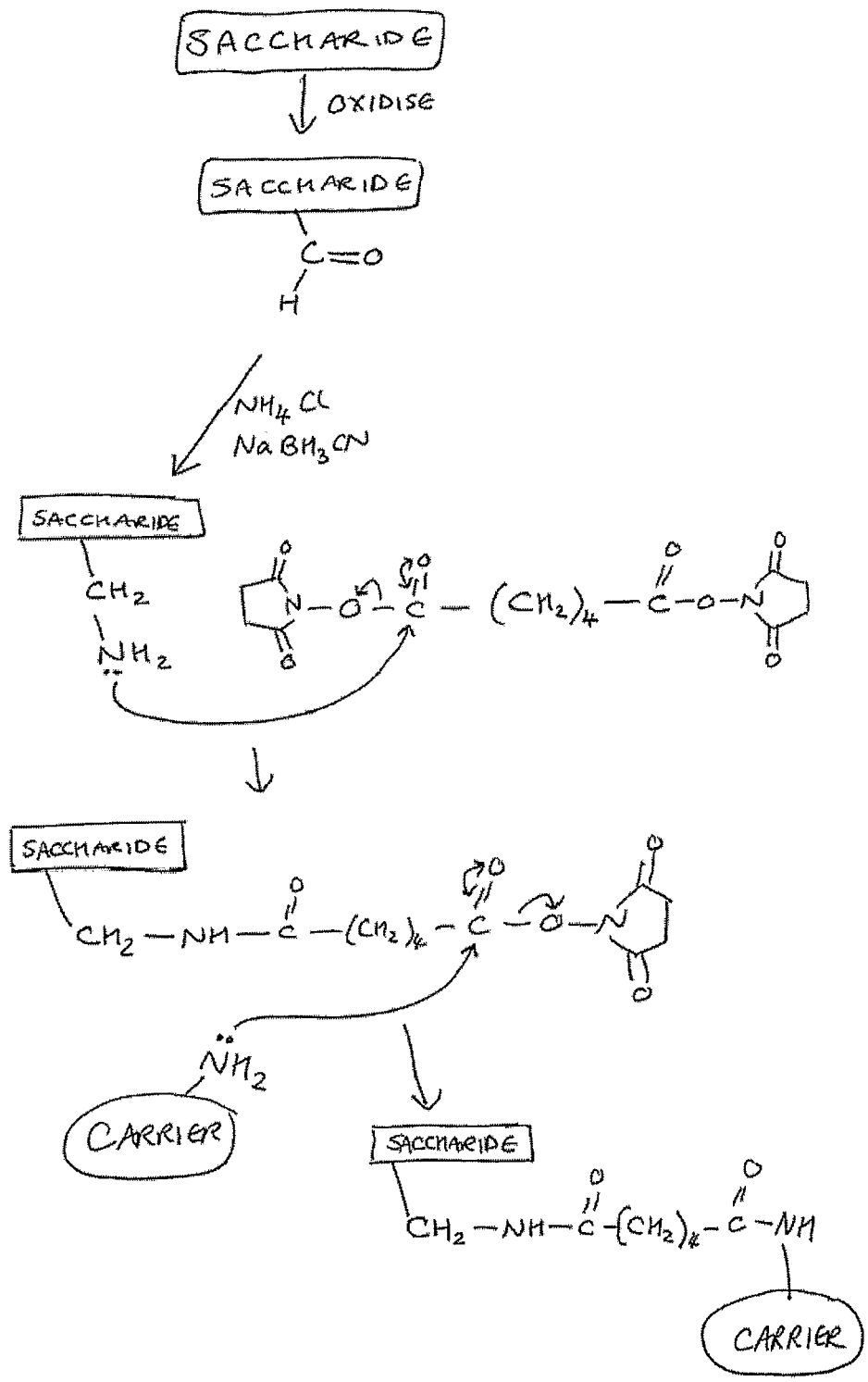
FIG. 6 shows a preferred conjugation reaction using the succinimidyl diester of adipic acid, according to the first aspect of the invention.
Figure 7:
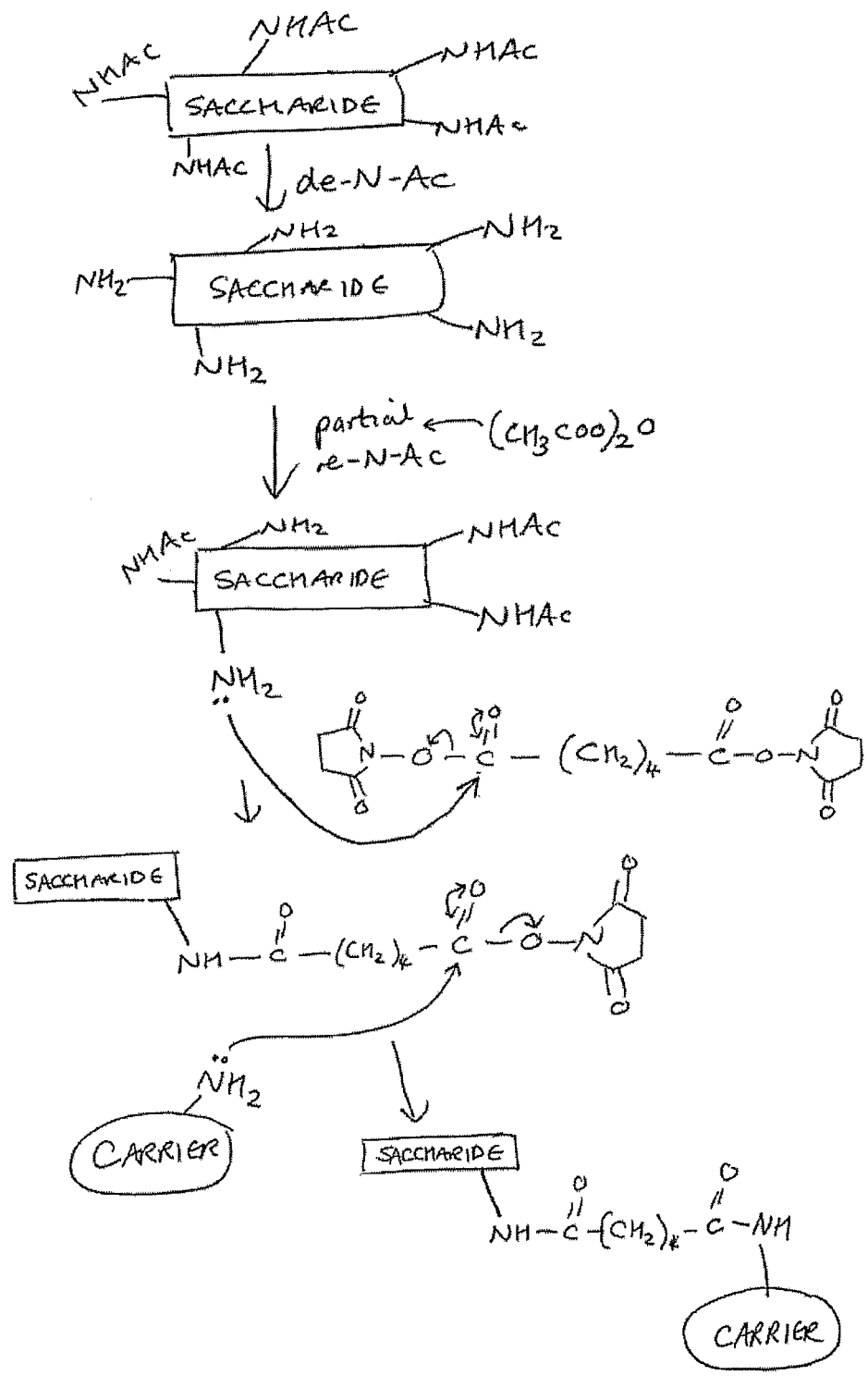
FIG. 7 shows a preferred conjugation reaction using the succinimidyl diester of adipic acid, according to the second aspect of the invention.
Figure 8:
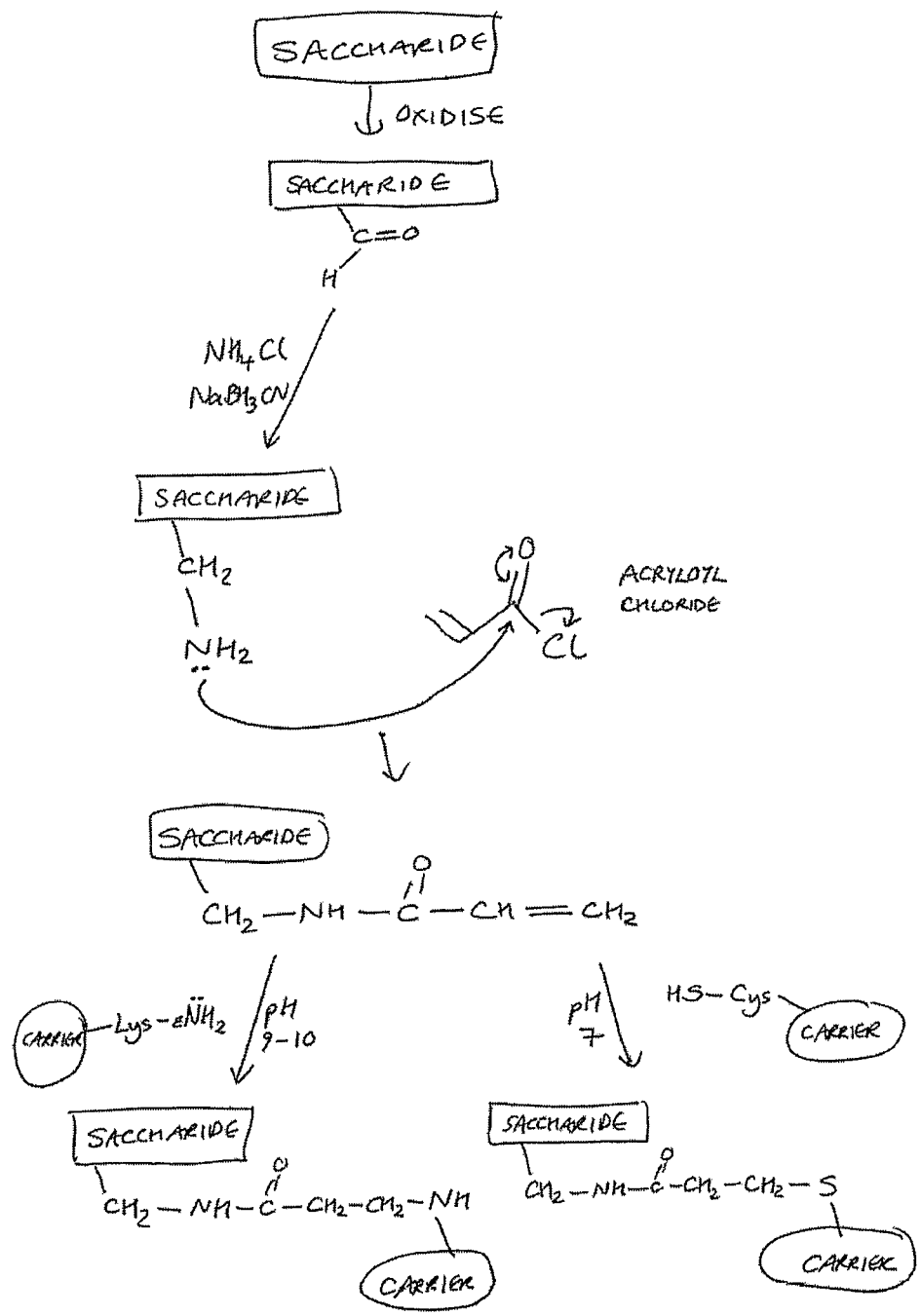
FIGS. 8 and 9 shows the use of (8) acryloylation and (9) a haloacylhalide, to prepare conjugates, after reductive amination of an aldehyde formed by oxidation of a terminal sialic acid residue.
Figure 9:
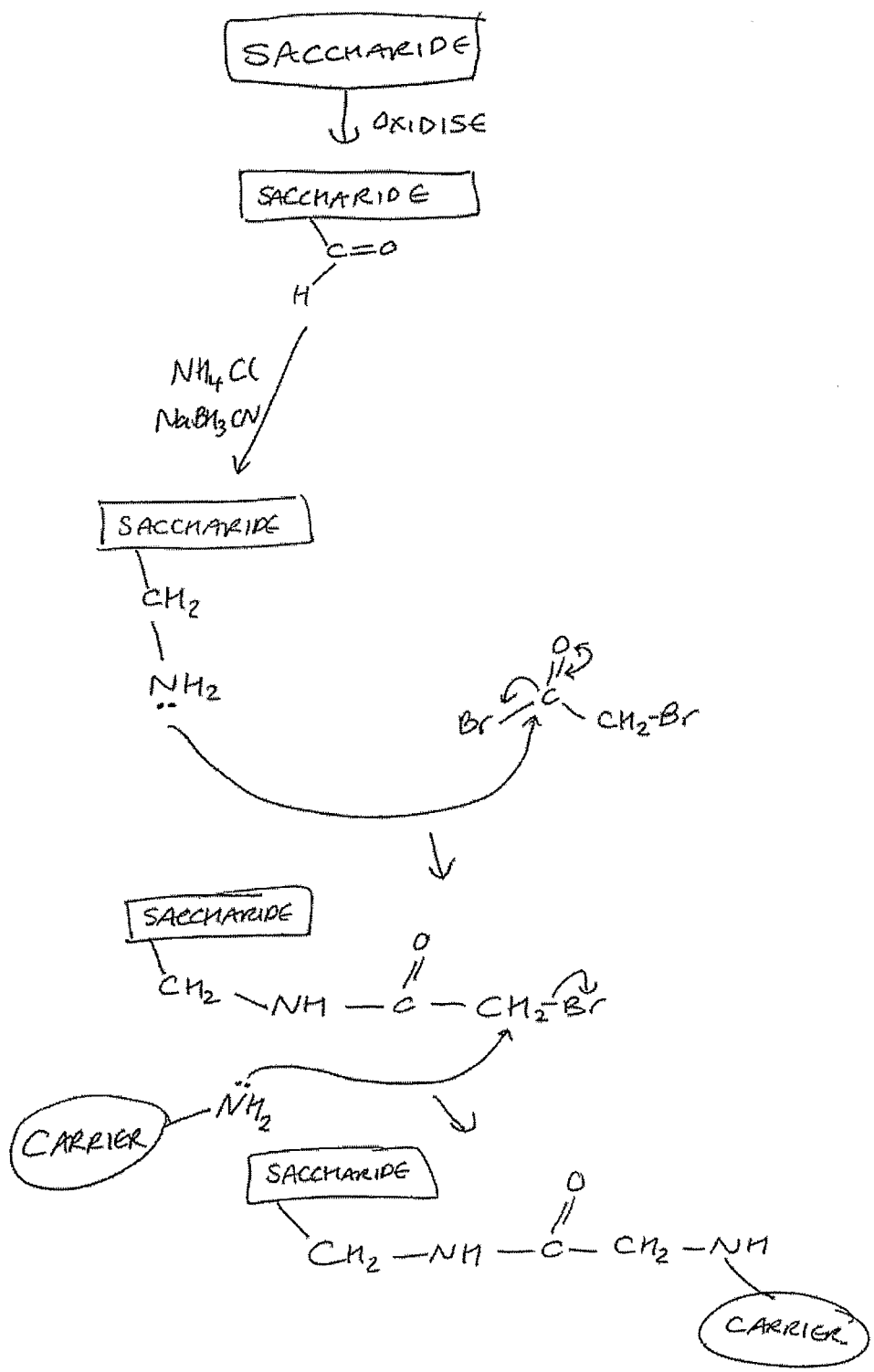

Capsular saccharide from GBS serotype Ib was purified as described in reference 15 and then re-acetylated as described above. The saccharide was de-N-acetylated to provide amine groups for linking. These amine groups were used to covalently conjugate the saccharides to monomeric tetanus toxoid (TT) either by direct reductive amination (on C8 of sialic acid, as described in the prior art) or via a SIDEA spacer (as described for meningococcal saccharides in ref. 218).

Sialic acid content in the conjugates was determined was performed according to the colorimetric method of ref. 219. The total saccharide amount was extrapolated from sialic acid content (sialic acids are on average 31% by weight of the polymer). Protein concentration in the conjugate was determined with the Micro BCA Protein Assay Kit (Pierce). A polysaccharide:protein weight ratio of between 1 and 4 was the target, and results were as follows:

| Conjugation | Saccharide (mg/ml) | Protein (mg/ml) | Ratio |
|---|---|---|---|
| Reductive amination | 1.740 | 1.271 | 1.37 |
| SIDEA spacer | 0.150 | 0.048 | 3.13 |

To investigate how the cross-linking ratio of conjugates could be affected, purified GBS Ia and Ib saccharides were subjected to varying degrees of oxidation and then conjugated to CRM197. Results were as follows

| % oxidation | Saccharide conc (mg/ml) | Protein conc (mg/ml) | Ratio (w/w) |
|---|---|---|---|
| Ia | | | |
| 5.0 | 1.188 | 0.468 | 2.54 |
| 14.2 | 1.360 | 0.776 | 1.75 |
| 44.7 | 1.018 | 0.690 | 1.48 |
| 79.0 | 2.989 | 2.012 | 1.49 |
| 86.0 | 1.737 | 1.074 | 1.62 |
| Ib | | | |
| 4.3 | 2.544 | 1.437 | 1.77 |
| 12.0 | 2.821 | 2.383 | 1.18 |
| 46.7 | 3.644 | 3.941 | 0.92 |
| 79.6 | 3.821 | 3.770 | 1.01 |
| 80.2 | 1.218 | 1.202 | 1.01 |

Similar experiments were used to study different protein carriers. CRM197 and tetanus toxoid were both used as carriers for GBS tVDe III saccharides and results were:

| % oxidation | Saccharide conc (mg/ml) | Protein conc (mg/ml) | Ratio (w/w) |
|---|---|---|---|
| CRM197 | | | |
| 4.3 | 3.270 | 1.150 | 2.84 |
| 17.5 | 4.130 | 2.894 | 1.43 |
| 40.9 | 3.056 | 1.822 | 1.68 |
| 61.8 | 3.165 | 2.358 | 1.34 |
| 78.9 | 4.230 | 4.502 | 0.94 |
| Tetanus toxoid | | | |
| 3.9 | 1.014 | 1.480 | 0.69 |
| 16.2 | 0.941 | 1.138 | 0.83 |
| 20.6 | 1.105 | 1.499 | 0.74 |
| 55.3 | 1.037 | 1.600 | 0.65 |

Three different carriers were compared for GBS type II and V saccharides: tetanus toxoid; CRM197; and human serum albumin. The degree of oxidation was 15.3% for the type V saccharide and 6.9% for the type II saccharide. Results were:

| Saccharide conc (mg/ml) | Protein conc (mg/ml) | Ratio (w/w) |
|---|---|---|
| II | | |
| 0.993 | 0.444 | 2.24 |
| 2.999 | 1.541 | 1.95 |
| 2.146 | 0.890 | 2.41 |
| V | | |
| 1.308 | 0.902 | 1.45 |
| 1.272 | 0.825 | 1.54 |
| 1.497 | 1.287 | 1.16 |

Human serum albumin was separately tested as a carrier for type Ia (6.7% oxidised), Ib (8.2% oxidised) and III (4.1% oxidised) saccharides:

| Type | Saccharide conc (mg/ml) | Protein conc (mg/ml) | Ratio (w/w) |
|---|---|---|---|
| Ia | 1.112 | 0.784 | 1.42 |
| Ib | 3.710 | 3.078 | 1.21 |
| III | 3.318 | 2.869 | 1.16 |

Conjugates of type Ia, Ib and III were made using four different carriers: tetanus toxoid; CRM197; GBS80; and GBS67. With the tetanus and CRM carriers the %s oxidation were 9.1% for Ia, 14.2% for Ib and 13% for III; with the GBS carriers the %s were 8.2%, 9.0% and 7.9%. Animals immunised with the conjugates were then tested for protection against the respective GBS types (i.e. homologous challenge), and results were as follows, expressed as the % of animals surviving lethal challenge:

| | TT | CRM197 | GBS80 | GBS67 | PBS control |
|---|---|---|---|---|---|
| Ia | 32 | 48 | 10 | 96 | 5 |
| Ib | 52 | 33 | 65 | 92 | 15 |
| III | 76 | 60 | 71 | 82 | 0 |

In parallel experiments, with challenge by a GBS type V strain but no immunisation with a type V saccharide, results were as follows:

| | TT | CRM197 | GBS80 | GBS67 | PBS control |
|---|---|---|---|---|---|
| V | 2 | 0 | 53 | 62 | 0 |

Thus the GBS carriers were able to provide some protection against the type V strain, and so the use of GBS proteins as carriers offers a background level of protein-mediated protection which can be supplemented by saccharides conjugated to the protein.

The level of free saccharide was tested for various conjugate lots, and results were as follows:

| GBS type | Carrier | free |
|---|---|---|
| Ia | CRM | <1.0% |
| | GBS80 | 3.5% |
| | GBS67 | <1% |

-continued

| GBS type | Carrier | free |
| --- | --- | --- |
| Ib | CRM | 1.8% |
|  | GBS80 | 14.8% |
|  | GBS67 | <1.0% |
| III | CRM | 1.6% |
|  | CRM | 4.4% |
|  | TetTox | 3.8% |
|  | GBS80 | 9.1% |
|  | GBS67 | <1.0% |

It will be understood that the invention has been described by way of example only and modifications may be made whilst remaining within the scope and spirit of the invention.

REFERENCES

The Contents of which are Hereby Incorporated by Reference

[1] Paoletti et al. (1990) *J Biol Chem* 265:18278-83.
[2] Wessels et al. (1990) *J Clin Invest* 86:1428-33.
[3] Paoletti et al. (1992) *Infect Immun* 60:4009-14.
[4] Paoletti et al. (1992) *J Clin Invest* 89:203-9.
[5] Wessels et al. (1987) *Proc Natl Acad Sci USA* 84:9170-4.
[6] Wang et al. (2003) *Vaccine* 21:1112-7.
[7] Wessels et al. (1993) *Infect Immun* 61:4760-6
[8] Wessels et al. (1995) *J Infect Dis* 171:879-84.
[9] Baker et al. (2004) *J Infect Dis* 189:1103-12.
[10] U.S. Pat. No. 4,356,170.
[11] Paoletti & Kasper (2003) *Expert Opin Biol Ther* 3:975-84.
[12] U.S. Pat. Nos. 6,027,733 & 6,274,144.
[13] worldwideweb.polymer.de
[14] Lewis et al. (2004) *PNAS USA* 101:11123-8.
[15] International patent application PCT/IB2006/000626 (published as WO 2006/082527 A2), 'PURIFICATION OF STREPTOCOCCAL CAPSULAR POLYSACCHARIDE', claiming priority from GB-0502096.1 (CHIRON SRL).
[16] Ramsay et al. (2001) *Lancet* 357(9251):195-196.
[17] Lindberg (1999) *Vaccine* 17 Suppl 2:S28-36.
[18] Buttery & Moxon (2000) *J R Coll Physicians Lond* 34:163-168.
[19] Ahmad & Chapnick (1999) *Infect Dis Clin North Am* 13:113-33, vii.
[20] Goldblatt (1998) *J. Med. Microbiol.* 47:563-567.
[21] European patent 0477508.
[22] U.S. Pat. No. 5,306,492.
[23] WO98/42721.
[24] Dick et al. in *Conjugate Vaccines* (eds. Cruse et al.) Karger, Basel, 1989, 10:48-114.
[25] Hermanson *Bioconjugate Techniques*, Academic Press, San Diego (1996) ISBN: 0123423368.
[26] Anonymous (January 2002) *Research Disclosure*, 453077.
[27] Anderson (1983) *Infect Immun* 39(1):233-238.
[28] Anderson et al. (1985) *J Clin Invest* 76(1):52-59.
[29] EP-A-0372501.
[30] EP-A-0378881.
[31] EP-A-0427347.
[32] WO93/17712
[33] WO94/03208.
[34] WO98/58668.
[35] EP-A-0471177.
[36] WO91/01146

[37] Falugi et al. (2001) *Eur J Immunol* 31:3816-24.
[38] Baraldo et al. (2004) *Infect Immun* 72:4884-87.
[39] EP-A-0594610.
[40] WO00/56360.
[41] WO02/091998.
[42] Kuo et al. (1995) *Infect Immun* 63:2706-13.
[43] WO01/72337
[44] WO00/61761.
[45] WO99/42130.
[46] WO2004/011027.
[47] WO96/40242.
[48] Lei et al. (2000) *Dev Biol (Basel)* 103:259-264.
[49] WO00/38711; U.S. Pat. No. 6,146,902.
[50] WO94/06467.
[51] U.S. Pat. No. 6,248,570.
[52] Wessels et al. (1989) *Infect Immun* 57:1089-94.
[53] U.S. Pat. No. 4,711,779.
[54] WO00/10599.
[55] U.S. Pat. No. 4,057,685.
[56] WO99/24578.
[57] WO99/36544.
[58] WO99/57280.
[59] WO00/22430.
[60] Tettelin et al. (2000) *Science* 287:1809-1815.
[61] WO96/29412.
[62] Pizza et al. (2000) *Science* 287:1816-1820.
[63] WO01/52885.
[64] Bjune et al. (1991) *Lancet* 338(8775):1093-1096.
[65] Fukasawa et al. (1999) *Vaccine* 17:2951-2958.
[66] Rosenqvist et al. (1998) *Dev. Biol. Stand.* 92:323-333.
[67] Costantino et al. (1992) *Vaccine* 10:691-698.
[68] WO03/007985.
[69] Watson (2000) *Pediatr Infect Dis J* 19:331-332.
[70] Rubin (2000) *Pediatr Clin North Am* 47:269-285, v.
[71] Jedrzejas (2001) *Microbiol Mol Biol Rev* 65:187-207.
[72] Bell (2000) *Pediatr Infect Dis J* 19:1187-1188.
[73] Iwarson (1995) *APMIS* 103:321-326.
[74] Gerlich et al. (1990) *Vaccine* 8 Suppl:S63-68 & 79-80.
[75] Hsu et al. (1999) *Clin Liver Dis* 3:901-915.
[76] Gustafsson et al. (1996) *N. Engl. J. Med.* 334:349-355.
[77] Rappuoli et al. (1991) *TIBTECH* 9:232-238.
[78] *Vaccines* (2004) eds. Plotkin & Orenstein. ISBN 0-7216-9688-0.
[79] WO02/02606.
[80] Kalman et al. (1999) *Nature Genetics* 21:385-389.
[81] Read et al. (2000) *Nucleic Acids Res* 28:1397-406.
[82] Shirai et al. (2000) *J. Infect. Dis.* 181(Suppl 3):S524-S527.
[83] WO99/27105.
[84] WO00/27994.
[85] WO00/37494.
[86] WO99/28475.
[87] Ross et al. (2001) *Vaccine* 19:4135-4142.
[88] Sutter et al. (2000) *Pediatr Clin North Am* 47:287-308.
[89] Zimmerman & Spann (1999) *Am Fam Physician* 59:113-118, 125-126.
[90] Dreesen (1997) *Vaccine* 15 Suppl:S2-6.
[91] *MMWR Morb Mortal Wkly Rep* 1998 Jan. 16; 47(1):12, 19.
[92] McMichael (2000) *Vaccine* 19 Suppl 1:S101-107.
[93] WO02/34771.
[94] Dale (1999) *Infect Dis Clin North Am* 13:227-43, viii.
[95] Ferretti et al. (2001) *PNAS USA* 98: 4658-4663.
[96] Kuroda et al. (2001) *Lancet* 357(9264):1225-1240; see also pages 1218-1219.
[97] Robinson & Torres (1997) *Seminars in Immunology* 9:271-283.

[98] Donnelly et al. (1997) *Annu Rev Immunol* 15:617-648.
[99] Scott-Taylor & Dalgleish (2000) *Expert Opin Investig Drugs* 9:471-480.
[100] Apostolopoulos & Plebanski (2000) *Curr Opin Mol Ther* 2:441-447.
[101] Ilan (1999) *Curr Opin Mol Ther* 1:116-120.
[102] Dubensky et al. (2000) *Mol Med* 6:723-732.
[103] Robinson & Pertmer (2000) *Adv Virus Res* 55:1-74.
[104] Donnelly et al. (2000) *Am J Respir Crit. Care Med* 162(4 Pt 2):S190-193.
[105] Davis (1999) *Mt. Sinai J. Med.* 66:84-90.
[106] Paoletti et al. (2001) *Vaccine* 19:2118-2126.
[107] WO00/56365.
[108] Gennaro (2000) *Remington: The Science and Practice of Pharmacy.* 20th edition, ISBN: 0683306472.
[109] WO03/009869.
[110] Almeida & Alpar (1996) *J. Drug Targeting* 3:455-467.
[111] Agarwal & Mishra (1999) *Indian J Exp Biol* 37:6-16.
[112] WO00/53221.
[113] Jakobsen et al. (2002) *Infect Immun* 70:1443-1452.
[114] Bergquist et al. (1998) *APMIS* 106:800-806.
[115] Baudner et al. (2002) *Infect Immun* 70:4785-4790.
[116] Ugozzoli et al. (2002) *J Infect Dis* 186:1358-1361.
[117] *Vaccine Design* . . . (1995) eds. Powell & Newman. ISBN: 030644867X. Plenum.
[118] WO00/23105.
[119] WO90/14837.
[120] Podda (2001) *Vaccine* 19:2673-80.
[121] Frey et al. (2003) *Vaccine* 21:4234-7.
[122] U.S. Pat. No. 6,299,884.
[123] U.S. Pat. No. 6,451,325.
[124] U.S. Pat. No. 5,057,540.
[125] WO96/33739.
[126] EP-A-0109942.
[127] WO96/11711.
[128] WO00/07621.
[129] Barr et al. (1998) *Advanced Drug Delivery Reviews* 32:247-271.
[130] Sjolanderet et al. (1998) *Advanced Drug Delivery Reviews* 32:321-338.
[131] Niikura et al. (2002) *Virology* 293:273-280.
[132] Lenz et al. (2001) *J Immunol* 166:5346-5355.
[133] Pinto et al. (2003) *J Infect Dis* 188:327-338.
[134] Gerber et al. (2001) *Virol* 75:4752-4760.
[135] WO03/024480
[136] WO03/024481
[137] Gluck et al. (2002) *Vaccine* 20:B10-B16.
[138] EP-A-0689454.
[139] Johnson et al. (1999) *Bioorg Med Chem Lett* 9:2273-2278.
[140] Evans et al. (2003) *Expert Rev Vaccines* 2:219-229.
[141] Meraldi et al. (2003) *Vaccine* 21:2485-2491.
[142] Pajak et al. (2003) *Vaccine* 21:836-842.
[143] Kandimalla et al. (2003) *Nucleic Acids Research* 31:2393-2400.
[144] WO02/26757.
[145] WO99/62923.
[146] Krieg (2003) *Nature Medicine* 9:831-835.
[147] McCluskie et al. (2002) *FEMS Immunology and Medical Microbiology* 32:179-185.
[148] WO98/40100.
[149] U.S. Pat. No. 6,207,646.
[150] U.S. Pat. No. 6,239,116.
[151] U.S. Pat. No. 6,429,199.
[152] Kandimalla et al. (2003) *Biochemical Society Transactions* 31 (part 3):654-658.
[153] Blackwell et al. (2003) *J Immunol* 170:4061-4068.
[154] Krieg (2002) *Trends Immunol* 23:64-65.
[155] WO01/95935.
[156] Kandimalla et al. (2003) *BBRC* 306:948-953.
[157] Bhagat et al. (2003) *BBRC* 300:853-861.
[158] WO03/035836.
[159] WO95/17211.
[160] WO98/42375.
[161] Beignon et al. (2002) *Infect Immun* 70:3012-3019.
[162] Pizza et al. (2001) *Vaccine* 19:2534-2541.
[163] Pizza et al. (2000) *Int J Med Microbiol* 290:455-461.
[164] Scharton-Kersten et al. (2000) *Infect Immun* 68:5306-5313.
[165] Ryan et al. (1999) *Infect Immun* 67:6270-6280.
[166] Partidos et al. (1999) *Immunol Lett* 67:209-216.
[167] Peppoloni et al. (2003) *Expert Rev Vaccines* 2:285-293.
[168] Pine et al. (2002) *J Control Release* 85:263-270.
[169] Domenighini et al. (1995) *Mol Microbiol* 15:1165-1167.
[170] WO99/40936.
[171] WO99/44636.
[172] Singh et al] (2001) *J Cont Release* 70:267-276.
[173] WO99/27960.
[174] U.S. Pat. No. 6,090,406
[175] U.S. Pat. No. 5,916,588
[176] EP-A-0626169.
[177] WO99/52549.
[178] WO01/21207.
[179] WO01/21152.
[180] Andrianov et al. (1998) *Biomaterials* 19:109-115.
[181] Payne et al. (1998) *Adv Drug Delivery Review* 31:185-196.
[182] Stanley (2002) *Clin Exp Dermatol* 27:571-577.
[183] Jones (2003) *Curr Opin Investig Drugs* 4:214-218.
[184] WO04/60308
[185] WO04/64759.
[186] WO99/11241.
[187] WO94/00153.
[188] WO98/57659.
[189] European patent applications 0835318, 0735898 and 0761231.
[190] Glezen & Alpers (1999) *Clin. Infect. Dis.* 28:219-224
[191] Madoff et al. (1994) *J Clin Invest* 94:286-92.
[192] Paoletti et al. (1994) *Infect Immun* 62:3236-43.
[193] WO03/093306.
[194] WO2004/018646.
[195] WO2004/041157.
[196] Geysen et al. (1984) *PNAS USA* 81:3998-4002.
[197] Carter (1994) *Methods Mol Biol* 36:207-23.
[198] Jameson, B A et al. 1988, *CABIOS* 4(1):181-186.
[199] Raddrizzani & Hammer (2000) *Brief Bioinform* 1(2):179-89.
[200] De Lalla et al. (1999) *J. Immunol.* 163:1725-29.
[201] Brusic et al. (1998) *Bioinformatics* 14(2):121-30
[202] Meister et al. (1995) *Vaccine* 13(6):581-91.
[203] Roberts et al. (1996) *AIDS Res Hum Retroviruses* 12(7):593-610.
[204] Maksyutov & Zagrebelnaya (1993) *Comput Appl Biosci* 9(3):291-7.
[205] Feller & de la Cruz (1991) *Nature* 349(6311):720-1.
[206] Hopp (1993) *Peptide Research* 6:183-190.
[207] Welling et al. (1985) *FEBS Lett.* 188:215-218.
[208] Davenport et al. (1995) *Immunogenetics* 42:392-297.
[209] Bodanszky (1993) *Principles of Peptide Synthesis* (ISBN: 0387564314).
[210] Fields et al. (1997) *Meth Enzymol* 289: Solid-Phase Peptide Synthesis. ISBN: 0121821900.

[211] Chan & White (2000) *Fmoc Solid Phase Peptide Synthesis*. ISBN: 0199637245.
[212] Kullmann (1987) *Enzymatic Peptide Synthesis*. ISBN: 0849368413.
[213] Ibba (1996) *Biotechnol Genet Eng Rev* 13:197-216.
[214] Qi Chen et al. (2002) *Infect Immun* 70:6409-15.
[215] Beckmann et al. (2002) *Infect Immun* 70:2869-76.
[216] Cheng et al. (2002) *Infect Immun* 70:2408-13.
[217] Cheng et al. (2001) *Infect Immun* 69:2302-8.
[218] WO03/007985.
[219] Svennerholm (1958) *Acta Chem. Scand.* 12:547-554.

The invention claimed is:

1. A process for preparing a conjugate of a *Streptococcus agalactiae* capsular saccharide and a carrier molecule, comprising the steps of:
    (a) oxidising a *Streptococcus agalactiae* capsular saccharide in order to introduce an aldehyde group into between 5% and 50% of the total galactose monosaccharide units in the saccharide to give modified galactose residues, wherein the modified galactose residues are modified by conversion of galactose to galactohexodialose, and wherein sialic acid residues of the capsular saccharide are retained; and
    (b) coupling at least one modified galactose residue to a carrier molecule.

2. The process of claim 1 wherein, after conjugation, free and conjugated saccharides are separated.

3. The process of claim 1 wherein the conjugate has a saccharide:protein ratio (w/w) of between 1:5 and 5:1.

4. The process of claim 1 wherein the saccharide has a molecular weight>30 kpa.

5. The process of claim 1, further comprising the step of
    (c) providing a lyophilised pharmaceutical composition comprising the conjugate and a pharmaceutically acceptable carrier.

6. The process of claim 1 wherein the saccharide is from one of GBS serotypes Ia, Ib, II, III, or V.

7. The process of claim 1 wherein the saccharide is shorter than native capsular saccharide.

8. The process of claim 1 wherein the saccharide is partially or fully de-O-acetylated.

9. The process of claim 1 wherein the saccharide is partially or fully de-N-acetylated.

10. The process of claim 1 wherein the carrier is a bacterial toxin or toxoid.

11. The process of claim 1 wherein the carrier is attached to the saccharide via a —$NH_2$ group in the carrier.

12. The process of claim 1 wherein attachment to the carrier is based on reductive amination involving an oxidised galactose in the saccharide, from which an aldehyde is formed, and an amine in a linker.

13. The process of claim 1 wherein attachment to the carrier is based on reductive amination involving an oxidised galactose in the saccharide, from which an aldehyde is formed, and an amine in the carrier.

14. The process of claim 12 or claim 13 wherein the saccharide is re-N-acetylated prior to reductive amination.

15. The process of claim 14 wherein the saccharide is re-N-acetylated prior to prior to oxidation of galactose.

16. The process of claim 1 wherein an individual saccharide is attached to multiple carriers.

17. The process of claim 1 wherein the carrier molecule is CRM197.

18. The process of claim 2 wherein the carrier molecule is CRM197.

* * * * *

UNITED STATES PATENT AND TRADEMARK OFFICE
CERTIFICATE OF CORRECTION

PATENT NO. : 8,513,392 B2  Page 1 of 1
APPLICATION NO. : 11/883614
DATED : August 20, 2013
INVENTOR(S) : Francesco Berti It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1388 days.

Signed and Sealed this

Fifteenth Day of September, 2015

Michelle K. Lee
*Director of the United States Patent and Trademark Office*